(12) United States Patent
Souza Dos Santos et al.

(10) Patent No.: US 8,586,054 B2
(45) Date of Patent: Nov. 19, 2013

(54) METHOD FOR MODULATING, TREATING AND/OR PREVENTING METABOLIC SYNDROME USING MAS-G-PROTEIN-COUPLED RECEPTOR AGONISTS

(75) Inventors: Robson Augusto Souza Dos Santos, Belo Horizonte (BR); Sergio Henrique Sousa Santos, Belo Horizonte (BR); Jaqueline Isaura Alvarez Leite, Belo Horizonte (BR); Marina Matos De Moura, Belo Horizonte (BR); Andrea Siqueira Haibara, Belo Horizonte (BR); Luciana Rodriques Fernandez, Belo Horizonte (BR); Michael Bader, Berlin (DE); Natalia Alenina, Berlin (DE); Rubens Dario Sinisterra, Belo Horizonte (BR)

(73) Assignees: Max-Delbruck-Centrum fur Molekulare Medizin, Berlin (DE); Universidade Federal de Minas Gerais, Belo Horizonte (BR)

( * ) Notice: Subject to any disclaimer, the term of this patent is extended or adjusted under 35 U.S.C. 154(b) by 0 days.

(21) Appl. No.: 12/298,351

(22) PCT Filed: Apr. 26, 2007

(86) PCT No.: PCT/BR2007/000100
§ 371 (c)(1),
(2), (4) Date: Mar. 31, 2009

(87) PCT Pub. No.: WO2007/121546
PCT Pub. Date: Nov. 1, 2007

(65) Prior Publication Data
US 2009/0221498 A1    Sep. 3, 2009

(30) Foreign Application Priority Data
Apr. 26, 2006  (BR) .................................. 0602366

(51) Int. Cl.
*A61K 38/04* (2006.01)
*A61K 38/00* (2006.01)

(52) U.S. Cl.
USPC ..................................... 424/198.1; 514/16

(58) Field of Classification Search
None
See application file for complete search history.

(56) References Cited

U.S. PATENT DOCUMENTS 6,235,766 B1    5/2001   Heitsch et al.

FOREIGN PATENT DOCUMENTS

| WO | WO 01/49744 | 7/2001 |
| WO | WO 03/039434 | 5/2003 |
| WO | WO 2007/000036 | 1/2007 |

OTHER PUBLICATIONS

Santos et al., Angiotensin-(1-7) is an endogenous ligand for the G protein-coupled receptor Mas. Proc. Natl. Acad. Sci. USA 100:8258-8263, 2003.*
Santos et al., "Angiotensin-(1-7): blood, heart, and blood vessels," *Current Medicinal Chemistry, Cardiovascular and Hematological Agents*, Oct. 2005, vol. 3, No. 4, pp. 383-391.
Walther et al., "Altered heart rate and blood pressure variability in mice lacking the *Mas* protooncogene," *Brazilian Journal of Medical and Biological Research*, 2000, vol. 33, pp. 1-9.

* cited by examiner

*Primary Examiner* — Ruixiang Li
(74) *Attorney, Agent, or Firm* — Saliwanchik, Lloyd & Eisenschenk

(57) ABSTRACT

The present invention is characterized by the use of Mas-G-protein-coupled receptor agonists for the control, prevention and treatment of the body levels of triglycerides, cholesterol and glucose, as well as of hyper-tension and possible increase in body weight, which are characteristic of the clinical manifestation of the metabolic syndrome and its complications. Another characteristic of the invention is the use of Mas-G-protein-coupled receptor agonists, including the Angiotensin-(1-7) peptide and its analogs, agonists, either peptidic or non-peptidic, as modulators of the manifestations of insulin resistance and glucose intolerance and in the prevention and treatment of the related alterations. The invention claims the use of MAS-G-protein-coupled receptor agonists, formulated with pharmaceutically and pharmacologically acceptable excipients or carriers, and Mas-G-protein-coupled receptor agonists, including the Angiotensin-(1-7) peptide and its analogs, agonists, either peptidic or non-peptidic, as modulators of the metabolic syndrome, the diseases that compose it and its complications.

7 Claims, 13 Drawing Sheets a)

b)

a: Retroperitoneal fat
b: Epididymal fat c)

WT FVB/N      KO Mas FVB/N

B-Act

Glut 4

WT FVB/N      KO Mas FVB/N

Angiotensinogen mRNA

TGF-β mRNA

Mas receptor expression in rat and mice adipose tissue

1- Marker
2- Adipose Tissue -Mice
3- Adipose Tissue - Rat
4- Positive Control Testis

METHOD FOR MODULATING, TREATING AND/OR PREVENTING METABOLIC SYNDROME USING MAS-G-PROTEIN-COUPLED RECEPTOR AGONISTS

This application is a National Stage Application of International Application Number PCT/BR2007/000100, filed Apr. 26, 2007; which claims priority to Brazil Patent Application No. PI0602366-5, filed Apr. 26, 2006, all of which are incorporated herein in their entirety.

The present invention relates to the use of MAS-G-protein-coupled receptor agonists as a mechanism of control, prevention and treatment of triglycerides, cholesterol and glucose levels in the body, as well as of the control over the increase in body weight and hypertension, characteristics of the manifestation of the metabolic syndrome and its complications.

Another characteristic of the invention relates to the use of MAS-G-protein-coupled receptor agonists, including the angiotensin-(1-7) peptide and its analogs, agonists, either peptidic or non-peptidic, as modulators of the manifestations of resistance to insulin and intolerance to glucose, and in the prevention and treatment of the related alterations and diseases.

The invention furthermore relates to the use of MAS-G-protein-coupled receptor agonists, formulated with pharmaceutically and pharmacologically acceptable excipients or carriers, and MAS, G-protein-coupled receptor agonists, including the angiotensin-(1-7) peptide and its analogs, agonists, either peptidic or non-peptidic, as modulators of the metabolic syndrome, the diseases that compose it and its complications.

The metabolic syndrome, also known as insulin-resistance syndrome, is characterized by the variable coexistence of obesity, hyperinsulinemia, dislipidemy and hypertension. Other findings include proinflammatory state, microalbuminuria and hypercoagulability. The set of risk factors that identify the metabolic syndrome was recognized for the first time in 1983. In 1988, Reaven introduced the term X syndrome and identified the resistance to insulin, defined as the smallest capitation of glucose by the peripheral tissues, as the ordinary physiological substrate of the syndrome.

Other synonyms have been used for designating this constellation of risk factors (dislipidemia, resistance to insulin, hypertension and obesity), such as plurimetabolic syndrome, insulin-resistance syndrome and mortal quartet, among others [Miname M H; Chacra A P M. Síndrome Metabólica (Metabolic syndrome). Revista Sociedade Cardiol. Est. São Paulo 6:482-489, 2005].

In 1998, the World Health Organization established the unified term metabolic syndrome, since studies did not identify the presence of resistance to insulin as a single causal factor of all the components of the syndrome. The pathogenesis of the syndrome is multifactorial, obesity, sedentary life, diet and interaction with genetic factors being responsible for the appearance there of. Mutations and polymorphisms in the genes associated with resistance to insulin, abnormalities in the adipocytes, hypertension and lipidic alterations play a central role in the etiopathogeny of the syndrome.

The diagnosis of the metabolic syndrome seems to identify patients with an additional cardiovascular risk with respect to the classic risk factors. In 2001, the "Third Report of the National Cholesterol Education Program Expert Panel on Detection, Evaluation and Treatment of High Blood Cholesterol in Adults "(NCEP-ATPPIII) [Executive Summary of The Third Report of the National Cholesterol Education Program Expert Panel on Detection, Evaluation and Treatment of High Blood Cholesterol in Adults (Adult Treatment Panel III). JAMA 2001; 285:2486-97], proposed the diagnostic criteria for the metabolic syndrome, based on five parameters: abdominal circumference, triglycerides, high-density lipo-protein (HDL-cholesterol), blood pressure and fasting glycemia [Miname M H; Chacra A P M. Síndrome Metabólica (Metabolic syndrome). Revista Sociedade CArdiol Est. São Paulo 6:482-489, 2005].

Dislipidemia, the main alteration encountered in the metabolic syndrome, is characterized by an increase in the circulating free fatty acids and by the rise in triglycerides (inadequate esterification). Another alteration is a failure of the adipocytes in retaining the free fatty acids inside them, increasing the flow thereof to the circulation. This mechanism is facilitated by the resistance to insulin. These alterations increase the amount of free fatty acids to the liver.

In the resistance to insulin, the liver stimulates the hepatic synthesis of triglycerides, since it promotes the re-esterification of these fatty acids, forming triglycerides, which are released into the circulation in the form of very low density lipoproteins (VLDL) [Miname M H; Chacra A P M. Síndrome Metabólica (Metabolic syndrome). Revista Sociedade CArdiol. Est. São Paulo 6:482-489, 2005].

The renin-angiotensin-system (RAS) constitutes a coordinated hormonal cascade that is initiated by the biosynthesis of the renin enzyme by the juxtaglomerular cells of the renal arterioles. Renin is then released by these cells through exocytosis, acting enzymatically on the angiotensinogen (AGT), cleaving it to an inactive decapeptide, angiotensin I (Ang I), which in turn will be catabolized by the angiotensin converting enzyme (ACE) into an octapeptide that is biologically active, angiotensin II (Ang II).

Renin does not have a direct biological (non-enzymatic) action, but its receptor has been recently identified, which exerts direct biological actions [Nguyen, G. et al (1996). Specific receptor binding of renin on human mesangial cells in culture increases plasminogen activator inhibitor 1 antigen. Kidney Int. 50, 1897-1903; Nguyen, G. et al (2002) Pivotal role of the renin/prorenin receptor in angiotensin II production and cellular responses to renin. J. Clin Invest. 109, 1417-11427]. Other enzymes act on the AGT to form Ang II (catepsins and kimases), joining the renin in this catalysis.

The RAS (renin-angiotensin system) has been recognized as an important regulator of the systemic blood pressure and of the renal hydroelectrolytic balance. In the past decade, a number of components of this system were identified in adrenal glands, kidneys, brain, heart and blood vessels. Recently, substantial data indicate the presence of components of the RAS in the adipose [Massiera F, Seydoux J. Geloen A et al Angiotensin-deficient mice exhibit impairment of diet induced weight gain with alteration in adipose tissue development and increased locomotor activity. Endocrinology 142:5220-5225, 2001].

Besides, the local RAS has been implied as co-adjuvant in pathologic processes through the modulation of the genetic expression, of the growth, fibrosis and possibly of the inflammatory response. Some components of the RAS have already been identified in the adipocytes, such as: the AGT, renin, ACE, Ang Ii and the angiotensinergic receptors $AT_1$ and $AT_2$.

Among the metabolic alterations associated to the adipose tissue, one can point out: greater activity of plasma renin, higher plasma level of angiotensinogen, greater activity of the ACE, and a higher plasma level of aldosterone [Engeli S, Negrel Raymond, Sharma A Physiology of the adipose tissue renin-angiotensin system. Hypertension 35: 1270-1277, 2000]. The levels of mRNA of AGT are 60% higher in the adipose tissue than in the liver, considered so far the main source of substrate of the renin [Harp J B, DiGirolamo M. Components of the renin-angiotensin system in adipose tissue: changes with maturation and adipose mass enlargement. *J. Gerontol A Biol Sci Med. Sci.* 50: B270-276, 1995]. It has been demonstrated that the expression mRNA of the AGT is regulated by free fatty acids, and studies with Wistar-Kyoto rats have shown that the aging, generally associated with weight gain, resulted in the decreased expression of the AGT in the adipose tissue of these rats and of obese Wister rats, but not in Sprague-Dawley rats and in obese Zucker rats [Harp J B, DiGirolamo M. Components of the renin-angiotensin system in adipose tissue: changes with maturation and adipose mass enlargement. J. Gerontol A Biol Sci Med. Sci. 50: B270-276, 1995]; Giacchetti G, Faloia E, Sardu C, et al. Different gene expression of the RAS in human subcutaneous and visceral adipose tissue: *Intern J Obes Relat Metab Discord.* 23 (suppl 5): S71, 1999. Abstract].

In addition, the expression of AGT is higher in visceral adipocytes than in subcutaneous adipocytes in these types of rats, as well as in the human species [Safonova I, Aubert J, Negrel R, Aihaud G. Regulation by fatty acids of angiotensinogen gene expression in preadipose cells. *Biochem J* 322: 235-239, 1997].

A positive relation between levels of AGT in the plasma and the pressoric levels was first described in 1979 by Walker et al [Walker W G, Whelton P K, Saito H, Russel R P, Hermann J. Relation between blood pressure and renin, renin substrate, angiotensin II, aldosterone and urinary sodium and potassium in 574 ambulatory subjects. *Hypertension* 1:287-291, 1979] and has been confirmed, not only in human beings [Caulfield M, Lauvender P, Newell-Priced J, Jamdar S, Farrall M, Clark A J L. Angiotensinogen in human essential hypertension. *Hypertension* 28: 1123-1125, 1996], but also in models of sporadically hypertensive rats [Nyhui N, Tamura K, Yamaguchi S, et al. Tissue Angiotensinogen gene expression induced by lipopolysaccharide in hypertensive rats. *Hypertension* 30:859-867, 1997; Alonso-Galicia M, Brands M W, Aappe D H, Hall J E. Hypertension in obese Zucker rats: role of angiotensin II and adrenergic activity. Hypertension 28: 1047-1054, 1996].

It is interesting to note that some studies have found positive correlation between the levels of plasma AGT and the body-mass index indifferent human populations. Also, one has already described the relation between obesity and polymorphism of AGT in a genetically isolated population. Not only the AGT, but also the activity of renin and the activity of plasma ACE, have been positively correlated to the body-mass index in obese subjects [Boustany C M, Bharadwaj K, et al Activation of the systemic and adipose renin-angiotensin system in rats with diet-induced obesity and hypertension. *Am J Physiol Regul Integr Corn Physiol* 287: 943-949, 2004]. These results have not been observed in obese Zucker rats; however, the infusion of Ang II lead to a more prominent increase in the blood pressure in obese rats if compared with the thin animals [Crandall D L, Herzlinlinger H E, Sauders B D, et al Developmental aspects of the adipose tissue renin-angiotensin system: therapeutic implications. *Drug Dev Res* 32: 117-125, 1994].

Ang II exerts its most potent and known effect (vasoconstriction) and others through the $AT_1$ receptor, but recently its second receptor, $AT_2$, has been characterized, in most cases proving to exert effects opposite the actions mediated via $AT_1$ receptor.

It was believed that Ang II was metabolized in fragments of biologically inactive peptides by circulation and tissular peptidases; however, studies have shown that at least three of these metabolic products exhibited a biological activity.

Ang II can be degraded to des-aspartic$^1$-ang II (Ang II), which is equipotent to Ang II in its interaction with the AT1 receptor, but has low efficacy in vivo due to its accelerated metabolism in the circulation. The second metabolic product of Ang II is the hexapeptide Ang IV, which has been demonstrated, in studies, to cause vasodilation and natriuresis ([Handa R. K. et al (2001) Autoradiographic analysis and regulation of angiotensin receptor subtypes AT (4), AT (1) and AT (1-7) IN THE KIDNEY. *Am. J. Physiol.* 281, F936-F947].

Angiotensin-(1-7) is the third and most promising metabolite of Ang II, since recent studies already indicate its possible therapeutic role ([Santos, R. A. S. et al (2005) Angiotensin-(1-7)) and its receptor as a target for new cardiovascular drugs. Expert Opin. Investig. Drugs 14(8), 1019-1031], and it is formed directly from Ang II or by parallel ways, by the action of the recently identified angiotensin II converting enzyme (ACE 2) [Donoghue, M. et al (2000) A novel angiotensin-converting enzyme related carboxypeptidase (ACE 2) converts angiotensin I to angiotensin (1-9). Circ. Res. 87, 1-9; Crackower, M. A. et al (2002) Angiotensin converting enzyme 2 is an essential regulator of heat function. Nature 417-822-828].

Ang (1-7) releases nitric oxide (NO) and prostaglandins ($PGI_2$) casing vasodilation, inhibiting the cellular proliferation and thrombogenesis ([Rajedran S, Chirkov Y Y, Campbell D J, Horowitz J D. Angiotensin-(1-7) enhances antiaggregatory effects of the nitric oxide donor sodium nitroprusside. *J. Cardiovasc Pharmacol* (46(4):459-463, 2005; Kucharewicz I, Pawlak R, Matys T et al. Antithrombotic effect of captopril and losartan is mediated by angiotensin-(1-7). Hypertension 40 (5):774-9, 2002] attenuating the vasoconstrictive effect of Ang II [Lemos V S, Cortes S F, Silva D M, CampagnoleSantos M J, Santos R A. Angiotensin-(1-7) is involved in the endothelium-dependent modulation of the phenylephrine-induced contraction in the aorta of mRen-2 transgenic rats. Br J Pharmacol 135 (7):1743-8, 2002; Clark M A, Diz D I, Tallant E A. Angiotensin-(1-7) downregulates the angiotensin II type I receptor in vascular smooth cells. Hypertension 37:1141-1146, 2001] and inhibiting the ACE [Deddish P A, Marcic B, Jackmann H L, et al. N-domain specific substrate and C-domain inhibitors of angiotensin-converting enzyme: angiotensin-(1-7) and Keto-ACE. Hypertension 31:912-917, 1998]. Instabilities in the harmonic interaction between Ang II and Ang-(1-7) seem to contribute to the beginning and development of pathologies.

The angiotensinergic receptors $AT_1$ and $AT_2$ of Ang II were identified in adipocytes of rats and humans, although the functionality of these needs to be better determined. In vivo, the expression of the gene for $AT_1$ in the adipose tissue seems to be dependent on the age, since one has observed a better density of $AT_1$ receptors in aged and obese Sprague-Dawley rats when compared with young and thin rats. Studies using adipose cell culture show that the AGT and the Ang II participate in the regulation and differentiation of the phenotype of the adipocyte. It is probable that the increase in the contents of triglycerides and in the activity of two lipolitic enzymes, fatty acid synthase and glycerol-3-phosphate dehydrogenase are mediated by Ang II, showing that this peptide controls adiposity by regulation of the synthesis and storage of lipids. In addition, Ang II participates in the release of norepinephrine by the sympathetic nervous system (SNS).

It has been demonstrated that the chronic infusion of Ang II results in an important reduction of weight and in the intake of foods, possibly by the greater release of norepinephrine, which would contribute to the increase in the metabolic activity and the rise in the consumption of energy. This effect of Ang II proved to be independent from the changes in the blood pressure and was abolished by losartan. Also, it was already seen that in culture of adipose cells, Ang II is an adipogenic factor, while in a live animal, it acts as an important reducer of weight and adipose mass. In addition to a significant relation between the artificial pressure, the body-mass index and the levels of the plasma AGT in normotensive and thin subjects [Engeli S, Negrel Raymond, Sharma A Physiology of the adipose tissue renin-angiotensin system. *Hypertension* 35: 1270-1277, 2000].

Studies report that approximately 20% of the variation of plasma AGT is liable to be explained by the levels of leptin present in the plasma. Taking plasma leptin as an indicator of the adipose tissue mass, this observation could be explained by the contribution of the adipose tissue to the levels of plasma AGT [Prasad A, Quyymi A Renin-angiotensin system and angiotensin receptor blocker in the metabolic syndrome. Circulation 110: 15071512, 2004]. However, the expression of AGT was not different in the adipose tissue of the obese subject if compared with thin subjects and obese subjects—hypertensive with normotensive obese subjects.

On the other hand, positive correlations were reported between the expression of AGT of the adipose tissue and the waist/hip relation, as well as between the secretion of AGT by isolated adipocytes and a set of adipocytes and body-mass index. Results of a recent research, in which one evaluated the relations between AGT, leptin and levels of blood pressure in a group of normotensive young men evidenced that the substrate of renin was significantly correlated with the body-mass index, plasma levels of leptin and blood pressure, in the subjects with a positive history for systemic arterial hypertension (SAH).

Thus, it was demonstrated that the circulating levels of AGT can contribute for the relation between the body weight and the blood pressure. Another factor evidenced was the relatively greater capacity of the visceral tissue in secreting the components of the RAS, which might be one more factor for justifying the greater cardiovascular risk associated to the central distribution of the fat ([Prasad A, Quyyumi A renin-angiotensin system and angiotensin receptor blockers in the metabolic syndrome. Circulation 110: 1507-1512, 2004].

Experimental studies suggest that the RAS of the adipose tissue, regulated by hormonal and nutritional factors, is influenced by the degree of obesity, and that Ang II can modulate the blood flow, growth factors and the local metabolism. Thus, the activation of the RAS can culminate in local and systemic deleterious effects on obese patients and can contribute to the appearance of the HAS and of the resistance to insulin on these patients. The resistance to insulin, in its turn, is associated with the reduction in the burning and increase in the release of the free fatty acids, which are converted in the liver into very low density lipoproteic (VLDL) particles rich in triglycerides.

Hypertriglyceridemia leads to a dislipidemic and highly atherogenic state, through the increase of the synthesis of easy-to-oxidize low density lipoproteic (LDL) particles and, at the same time, to the reduction of the high density lipoproteic (HDL) particles [Ginsberg H N. Insulin resistance and cardiovascular resistance. J Clin Invest 106: 453-458, 200]. However, the atherogenic profile evidenced in the carrier of the metabolic syndrome (MS) is the result of factors such as vascular dysfunction, a proinflammatory and procoagulating state, dislipidemia, HAS and insulin resistance.

Observational and prospective studies have suggested that the insulin resistance can have a crucial role to predict the incidence and the mortality related to cardiovascular diseases such as the coronary artery disease and encephalic vascular accident ([Ginsberg H N. Treatment of patients with the metabolic syndrome. Am J Cardiol 91 (suppl): 29E-39E, 2003]. Both in the insulin resistance state and in the metabolic syndrome, the endothelial dysfunction can be evidenced in an important way, being mainly accompanied by the reduction of the bioavailability in the NO.

In turn, the reduction of NO results in a greater production of reactive oxygen species (ROS), such as the superoxide ions ($O^{2-}$). The superoxide ions activate the NO to form peroxynitrite, which in turn uncouples the endothelial nitric oxide synthase by oxidation of its co-factor, tetrahydrobiopterin, which results in the production of more $O^{2-}$, instead of synthesis of NO. This cascade of events is called oxidative stress. In this way, the reduction of NO and of other relaxing factors derived from the endothelium can be accompanied by the increase in the production of endothelin, prostanoid vasoconstrictors and Ang II [Schiffrin E L: Beyond blood pressure: the endothelium and atherosclerosis progression. *AJH* 15: 115S-122-S,2002; Shinozaki K, Ayajiki K, Nishio Y, et al. Evidence for a causal role of the renin-angiotensin system in vascular dysfunction associated with insulin resistance *Hypertension* 43:255-262, 2004].

The reduction of bioavailability of NO was confirmed in experimental models of insulin resistance, wherein the following facts were observed: there is a correlation between the insulin sensitivity and the basal production of NO on healthful subjects. Insulin-resistant subjects present impaired an endothelium-dependent vasodilator response and the endothelial dysfunction can also be detected in healthful subjects with first degree of relationship with the type-2 diabetic subjects II [Schiffrin E L: Beyond blood pressure: the endothelium and atherosclerosis progression. *AJH* 15: 115S-122-S, 2002; Shinozaki K, Ayajiki K, Nishio Y, et al. Evidence for a causal role of the renin-angiotensin system in vascular dysfunction associated with insulin resistance *Hypertension* 43:255-262, 2004].

Therefore, the endothelial dysfunction seems to be a common link between the SAH, diabetes mellitus and the metabolic syndrome. It is known that the endothelium is a complex and dynamic organ, which presents vasoactive, vasoconstrictive substances such as Ang II and vasodilator substances such as Ang-(1-7) and NO. The vasoactive substances mediates the vascular tonus, structure and the function, influencing the growth of the vascular smooth muscle, apoptosis, platelet aggregation, adhesion of leucocytes and monocytes and thrombosis. The balance between the vasoconstrictive substances, the ones that generally induce the cellular growth, and the vasodilator substances, the ones that inhibit the cellular growth, is necessary for the maintenance of the normal vascular structure and its function. As was said before, within the RAS the vasodilator heptapeptide, Ang-(1-7) exerts an important counterregulatory role, opposing to most actions of Ang II via AT1 receptor, through its Mas, G-protein-coupled receptor [Santos R A S, Simoes e Silva A C, Maric C et al. Angiotensin-(1-7) is an endogenous ligand for the protein G-coupled receptor Mas. *Proc. Natl. Acd. Sci.* USA 100: 8258-8263, 2003]. Its expression has already been identified in the circulation, heart, blood vessels and kidneys. [Santos R A S, Campagnole-Santos M J, Andrade S P. Angiotensin-(1-7): an update. Reg Pept 91:45-62, 200].

Ang-(1-7) in most tissues acts directly through its Mas receptor [Santos R A S, Ferreira A J, Pinheiro S V B, et al. Angiotensin-(1-7) and its receptor as a potential target for new cardiovascular drugs. *Expert Opin. Investig. Drugs* 14(8): 1-13, 2005]. The physiological actions of Ang-(1-7) seem to modulate the actions of Ang II, especially in situations where the activity of Ang II is increased, as in the SAH. Therefore, the RAS is a dual, vasoconstrictive system, represented mainly by Ang II and, on the other hand, a vasodilator one having Ang-(1-7) as the most important agent.

Ang II is highly correlated with the endothelial dysfunction present in subjects who are hypertensive, diabetic, obese and have the metabolic syndrome. This peptide is implied in the cellular growth and in the inflammatory process evidenced in these subjects.

Thus, the oxidative stress caused by Ang II may result in an increase in the production of endothelin (ET-1), of the adhesion molecules such as the vascular cell adhesion molecule (VCAM-1) and the intercellular-1 adhesion molecule (ICAM-1), nuclear factor-k B (NF-kB), interleukin 6 (IL-6), among other inflammatory mediators. The activation of the NF-kB, in turn, promotes the synthesis of the type-1 plasminogen activator inhibitor (PAI-1), a natural inhibitor of the type-1 plasminogen activator in atheroclerotic vessels, resulting in damage to the fibrinolysis process [Gusik T J, Mussa S, Gastaldi D et al. Mechanisms of increased vascular superoxide production in human diabetes mellitus: role of NAD(P)H oxidase and endothelial nitric oxide synthase. *Circulation* 105: 1656-1662, 2002]. On patients having the metabolic syndrome, the levels of PAI1 and fibrinogen are high, the levels of PAI-1 being correlated with the levels of plasma insulin and with a degree of insulin resistance.

Thus, the PAI-1 seems to contribute as a factor predicting the appearance of diabetes mellitus (DM) on these patients. In addition, the coagulation disorder in the metabolic syndrome can be evidenced by the fact that the platelets exhibit resistance to the physiological actions of insulin, which is inhibitory of the platelet aggregation via release of NO.

However, the functional alterations of platelets and the activation of the coagulation cascade and of inflammation described above, provide the appearance of a prothrombotic and proinflammatory state, which may culminate in an atherosclerotic process on patients having the metabolic syndrome (Schiffrin E L. Beyond blood pressure: the endothelium and atherosclerosis progression. *AJH* 15: 115S-122-S, 2002].

In addition to the contribution of the RAS, mainly via Ang II, in the genesis of the metabolic syndrome already described above, interactions in different levels of this system with insulin have been implied as a fundamental factor in the development of DM and metabolic syndrome.

Evidences suggest that Ang II, via AT1 receptor, can modulate the actions of insulin. Thus, the RAS induces the appearance of resistance to the metabolic actions of insulin, causing hyperglycemia and rise in the cholesterol levels (VLDL) and triglycerides, and potentiates the proliferative effect of insulin. In addition, hyperglycemia and hyperinsulinemia activate the RAS through the increase in the expression of AGT, Ang II and AT1 receptors, which in turn can induce the appearance of arterial hypertension, cardiovascular and renal dysfunction [Engeli S, Schiling G P, Gorzeliniak K, et al. The adipose-tissue renin-angiotensin-aldosterone system: role in the metabolic syndrome? *Intern J f Biochem & Cell Biol* 35: 807-25, 2003].

Further, the oxidative stress caused mainly by Ang II via nicotinamide adenine dinucleotide phosphate-oxidase (ND-DPH) and NAD(P)H oxidase results in advanced glycation of amino acids in protein, lipids and nucleic acids.

As already described before, besides the synthesis of angiotensins, the adipose tissue has other secretory products that interfere directly with the regulation of blood pressure and/or tissular damage such as: leptin, TNF-alpha, PAI-1, TGF-β, resistin, adiponectin and others ([Blaj S, Stanciu S, Jurcut C, Ciobica L.; Hypertension in obese patients: a dysmetabolic hypertension with a possible adipocyte dysfunction mechanism. *Rom J Intern Med.;* 41(2): 1301-11, 2003].

Leptin influence the regulation of the blood pressure through various mechanisms such as: direct activation of the SNS and of the adrenal-pituitary axis, hydroelectrolytic balance, modulation of the endothelial function and alters the vascular remodeling.

Adiponectin, a protein expressed specifically in the adipocytes, is homologous to the type-VIII and type-X collagens and bonds to proteins of the proteic matrix, being therefore involved in injury and tissular repair processes. This protein, just as Ang II, increases the expression of TNF-alpha, through signaling mechanisms that involve the NF-kb [Ran J, Hirano T, Fukui T, Saito K, Kageyama H, Okada K, Adachi M; Angiotensin II infusion decreases plasma adiponectin level via its type 1 receptor in rats: an implication for hypertension-related insulin resistance. *Metabolism;* 55(4):478-88, 2006]. The concentrations of TNF-alpha and of resistin are involved with insulin resistance, endothelial dysfunction and with high concentrations of C-reactive protein and IL-6 found in obese people, predisposing these subjects to a greater morbidity and cardiovascular mortality.

These substances can interact with the RAS, reinforcing its actions, thus participating in the cardiovascular and renal alterations associated to obesity and to the metabolic syndrome.

U.S. Pat. No. 6,235,766 describes 1-(p-thienylbenzyl)imidazoles as agonists of angiotensin (1-7) receptors, processes for their preparation, their use, and pharmaceutical preparations comprising them. The imidazoles are described as potent, nonpeptide agonists of the postulated angiotensin (1-7) receptors, which are preferably located in the vessels (including endothelium), in the kidney, in the CNS, and in the heart, and can be used for the treatment and prophylaxis of high blood pressure, cardiac hypertrophy, cardiac insufficiency, coronary heart diseases such as angina pectoris, cardiac infarct, vascular restenosis after angioplasty, cardiomyopathies, endothelial dysfunction or endothelial damage, e.g., as a result of arteriosclerotic processes or diabetes mellitus, and also of arterial and venous thromboses.

However, in the prior art there is no application of the use of the MAS-G-protein-coupled agonists in the treatment of the metabolic syndrome, its components and its complications.

It is therefore an object of the present invention, to provide new strategies for the modulation, prevention or treatment of metabolic syndrome or its related complications in a subject.

According to a first aspect of the present invention, this object is solved by a method of modulating metabolic activities related to the clinical manifestation of the metabolic syndrome or its complications in a subject, comprising administering to said subject an effective amount of a MAS-G-protein-coupled receptor agonist.

A further preferred second aspect of the present invention then relates to a method for the prevention or treatment of diseases related to the metabolic syndrome or its complications in a subject, comprising administering to said subject an effective amount of a MAS-G-protein-coupled receptor agonist.

Preferably the clinical manifestations in method according to the present invention is selected from the group of alterations in the plasma or tissular levels of cholesterol, plasma or tissular levels of triglycerides, plasma or tissular levels of glucose, alterations in the body weight or in the blood pressure, high blood pressure, cardiac hypertrophy, cardiac insufficiency, coronary heart diseases such as angina pectoris, cardiac infarct, vascular restenosis after angioplasty, cardiomyopathies, an endothelial dysfunction or endothelial damage, e.g., as a result of atherosclerotic processes or in diabetes mellitus, and of arterial and venous thrombosis, obesity, the abdominal accumulation of body fat, and cardiac, renal, vascular, cerebral lesions and hormonal dysfunctions. Particularly preferred are the prevention and treatment of obesity and the abdominal accumulation of body fat.

The present invention particularly relates to a method which is characterized in that the MAS-G-protein-coupled receptor agonist is either peptidic or non-peptidic. Even more preferred examples are Mas-G-protein-coupled receptor agonists selected from an angiotensin-(1-7) peptide or an analog thereof or an 1-(p-thienylbenzyl)imidazole or an analog thereof.

Preferred compounds of the latter group are selected from 4-chloro-5-formyl-2-phenyl-1-[[4-[2-(n-butyloxycarbonylsulfonamido)-5-isobutyl-3-thienyl]phenyl]methyl]imidazole, 5-formyl-4-methoxy-2-phenyl-1-[[4-[2-(n-butyloxycarbonylsulfonamido)-5-isobutyl-3-thienyl]phenyl]methyl]imidazole, 5-formyl-4-methoxy-2-phenyl-1-[[4-[2-(n-propyloxycarbonylsulfonamido)-5-iso butyl-3-thienyl]phenyl]methyl]imidazole, 5-formyl-4-methoxy-2-phenyl-1-[[4-[2-(ethoxycarbonylsulfonamido)-5-isobutyl-3-thienyl]phenyl]methyl]imidazole, 5-formyl-4-methoxy-2-phenyl-1-[[4-[2-(methoxycarbonylsulfonamido)-5-isobutyl-3-thienyl]phenyl]methyl]imidazole, 5-formyl-4-methoxy-2-phenyl-1-[[4-[2-(n-butylaminocarbonylsulfonamido)-5-isobutyl-3-thienyl]phenyl]methyl]imidazole, 5-formyl-4-methoxy-2-phenyl-1-[[4-[2-(ethylaminocarbonylsulfonamido)-5-isobutyl-3-thienyl]phenyl]methyl]imidazole, 5-formyl-4-methoxy-2-phenyl-1-[[4-[2-(methylaminocarbonylsulfonamido)-5-isobutyl-3-thienyl]phenyl]methyl]imidazole, 5-formyl-4-methoxyethoxy-2-phenyl-1-[[4-[2-(n-butyloxycarbonylsulfonamido)-5-isobutyl-3-thienyl]phenyl]methyl]imidazole, 5-formyl-4-methoxy-2-phenyl-1-[[4-[2-(n-butyloxycarbonylsulfonamido)-5-isobutyl-3-thienyl]-2-chlorophenyl]methyl]imidazole, 5-formyl-4-methoxy-2-phenyl-1-[[4-[2-(n-butyloxycarbonylsulfonamido)-5-isobutyl-3-thienyl]-2-chlorophenyl]methyl]imidazole, 4-chloro-5-formyl-2-phenyl-1-[[4-[2-(n-butyloxycarbonylsulfonamido)-5-n-propyl-3-thienyl]phenyl]methyl]imidazole, 5-formyl-4-methoxy-2-phenyl-1-[[4-[2-(n-butyloxycarbonylsulfonamido)-5-n-propyl-3-thienyl]phenyl]methyl]imidazole, or a physiologically acceptable salt thereof; 5-formyl-4-methoxy-2-phenyl-1-[[4-[2-(methoxycarbonylsulfonamido)-5-n-propyl-3-thienyl]phenyl]methyl]imidazole, 5-formyl-4-methoxy-2-phenyl-1-[[4-[2-(n-butylaminocarbonylsulfonamido)-5-n-propyl-3-thienyl]phenyl]methyl]imidazole, or a physiologically acceptable salt thereof; 5-formyl-4-methoxy-2-phenyl-1-[[4-[2-(methylaminocarbonylsulfonamido)-5-n-propyl-3-thienyl]phenyl]methyl]imidazole, and physiologically acceptable salts of the above, 5-formyl-4-methoxy-2-phenyl-1-[[4-[2-(ethylaminocarbonylsulfonamido)-5-isobutyl-3-thienyl]phenyl]methyl]imidazole sodium salt; 5-formyl-4-methoxy-2-phenyl-1-[[4-[2-(ethylaminocarbonylsulfonamido)-5-isobutyl-3-thienyl]phenyl]methyl]imidazole L-lysine salt; and 5-formyl-4-methoxy-2-phenyl-1-[[4-[2-(ethylaminocarbonylsulfonamido)-5-isobutyl-3-thienyl]phenyl]methyl]imidazole tris(hydroxymethyl)aminomethane salt.

A further preferred aspect of the present invention then relates to a method according to the present invention which is characterized in that the Mas-G-protein-coupled receptor agonist is administered to said subject in the form of a pharmaceutical formulation via an oral, intramuscular, intravenous, subcutaneous, topical, transdermal, anal or inhalation route.

Thus, the forms of application described herein contain, but are not limited thereto, the use of MAS-G-protein-coupled receptor agonists and antagonists, including the angiotensin-(1-7) and its analogs, 1-(p-thienylbenzyl)imidazole and its analogs, agonists, either peptidic or non-peptidic and its formulations for use by the oral, intramuscular, endovenous, subcutaneous, topical, transdermal, anal, inhalation (pulmonary, intranasal, intrabuccal) application routes or as devices that may be implanted or injected for the prevention and treatment of diseases.

A further preferred aspect of the present invention then relates to a method according to the present invention which is characterized in that the Mas-G-protein-coupled receptor agonist is a nucleic acid encoding angiotensin-(1-7) or its analogs or a nucleic acid encoding Mas-G-protein-coupled receptor or its analogs.

According to the present invention, these nucleic acids can be used for gene therapy in order to provide, in particular endothelial cells with either a genetically encoded Mas-G-protein-coupled receptor agonist and/or nucleic acids that encode for Mas-G-protein-coupled receptor in order to increase the level of Mas-G-protein-coupled receptor in said cell as transformed. Preferably, said nucleic acid is operably linked to a genetic element that drives the expression thereof in the target cell or target tissue, where expression is desired. The nucleic acids can be provided using genetic vectors that are well known in the state of the art, such as, for example, adenoviral constructs, and the like. Furthermore, also the "naked" DNA can be used.

Pharmaceuticals employed according to the invention, which contain at least one agonist compound of the invention as the angiotensin-(1-7) peptide or 1-(p-thienylbenzyl)imidazole defined herein, and/or a physiologically tolerable salt thereof, can be administered enterally, for example orally or rectally, in the form of pills, tablets, film-coated tablets, sugar-coated tablets, granules, hard and soft gelatin capsules, solutions such as aqueous, alcoholic, or oily solutions, juices, drops, syrups, emulsions, or suspensions. Administration can also be carried out parenterally, for example subcutaneously, intramuscularly, or intravenously in the form of injection solutions or infusion solutions. Further possible administration forms are, for example, percutaneous or topical administration, in the form of ointments, creams, pastes, lotions, gels, sprays, powders, foams, aerosols, or solutions, or use in the form of implants. It is preferred that the pharmaceutical formulation is administered to said subject in the form of an implantable, injectable or orally administrable micro- and/or nanoparticulated device.

In a further aspect thereof, the present invention is directed at a method of isolating compounds interacting with Mas-G-protein-coupled receptor comprising the steps of: a) contacting Mas-G-protein-coupled receptor with at least one potentially interacting compound, and b) measuring binding of said compound to said Mas-G-protein-coupled receptor. This method is suitable for the determination of compounds that can interact with Mas-G-protein-coupled receptor and to identify, for example, activators, agonists, competitors or modulators of Mas-G-protein-coupled receptor, in particular activators, agonists, competitors or modulators of the enzymatic activity of the Mas-G-protein-coupled receptor. An example for such a preferred screening method is disclosed in Zhang et al. (Zhang R, Yan P K, Zhou C H, Liao J Y, Wang M W. Development of a homogeneous calcium mobilization assay for high throughput screening of mas-related gene receptor agonists. Acta Pharmacol Sin. 2007 January; 28(1): 125-31.) Another possibility would be the use of a phage-displayed random peptide library.

The potentially binding substance, whose binding to Mas-G-protein-coupled receptor is to be measured, can be any chemical substance or any mixture thereof. For example, it can be a substance of a peptide library, a combinatory library, a cell extract, in particular a plant cell extract, a "small molecular drug", a protein and/or a protein fragment.

The term "contacting" in the present invention means any interaction between the potentially binding substance(s) with Mas-G-protein-coupled receptor, whereby any of the two components can be independently of each other in a liquid phase, for example in solution, or in suspension or can be bound to a solid phase, for example, in the form of an essentially planar surface or in the form of particles, pearls or the like. In a preferred embodiment a multitude of different potentially binding substances are immobilized on a solid surface like, for example, on a compound library chip and the Mas-G-protein-coupled receptor or a part thereof is subsequently contacted with such a chip.

The Mas-G-protein-coupled receptor employed in a method of the present invention can be a full length protein or a fragment with N/C-terminal and/or internal deletion(s). Preferably the fragments are either N-terminal fragments comprising the enzymatic region of the protein or C-terminal fragments comprising the cytoplasmic region, depending on whether potentially interacting compounds are sought that specifically interact with the N- or C-terminal fragment.

Measuring of binding of the compound to Mas-G-protein-coupled receptor can be carried out either by measuring a marker that can be attached either to the Mas-G-protein-coupled receptor or to the potentially interacting compound. Suitable markers are known to someone of skill in the art and comprise, for example, fluorescence or radioactive markers. Further methods for detecting and/or measuring the binding of the two components to each other are known in the art and can without limitation also be used to measure the binding of the potential interacting compound to the Mas-G-protein-coupled receptor or Mas-G-protein-coupled receptor fragments. The effect of the binding of the compound or the activity of the Mas-G-protein-coupled receptor can also be measured indirectly, for example, by assaying the activity of the Mas-G-protein-coupled receptor after binding.

As a further step after measuring the binding of a potentially interacting compound and after having measured at least two different potentially interacting compounds at least one compound can be selected, for example, on grounds of the measured binding activity or on grounds of the detected increase or decrease of Mas-G-protein-coupled receptor activity.

The thus selected binding compound is then in a preferred embodiment modified in a further step. Modification can be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, iso-propyl, n-butyl, isobutyl, tert-butyl, n-pentyl or isopentyl groups, lower alkenyl groups, preferably having two to five carbon atoms, lower alkynyl groups, preferably having two to five carbon atoms or through the introduction of, for example, a group selected from the group consisting of $NH_2$, $NO_2$, OH, SH, NH, CN, aryl, heteroaryl, COH or COOH group. These modified compounds are regarded as "analogs" of the non-peptidic compounds according to the invention. The "analogs" of the peptidic compounds according to the invention can also be modified as described above, but are mainly differing in their amino acid composition (including modified amino acids). All analogs still exhibit some binding to the Mas-G-protein-coupled receptor protein as screened.

The thus modified binding substances are then individually tested with the method of the present invention, i.e. they are contacted with the Mas-G-protein-coupled receptor and subsequently binding of the modified compounds to the Mas-G-protein-coupled receptor is measured. In this step, both the binding per se can be measured and/or the effect of the function of the Mas-G-protein-coupled receptor like, e.g. the enzymatic activity of the Mas-G-protein-coupled receptor can be measured. If needed, the steps of selecting the binding compound, modifying the binding compound, contacting the binding compound with a Mas-G-protein-coupled receptor, and measuring the binding of the modified compounds to the Mas-G-protein-coupled receptor can be repeated a third or any given number of times as required. The above described method is also termed "directed evolution" since it involves a multitude of steps including modification and selection, whereby binding compounds are selected in an "evolutionary" process optimizing its capabilities with respect to a particular property, e.g. its binding activity, its ability to activate, or modulate the activity of the Mas-G-protein-coupled receptor.

In a further embodiment of the method of the present invention the interacting compound identified as outlined above, which may or may not have gone through additional rounds of modification and selection, is admixed with suitable auxiliary substances and/or additives. Such substances comprise pharmacological acceptable substances, which increase the stability, solubility, biocompatibility, or biological half-life of the interacting compound or comprise substances or materials, which have to be included for certain routs of application like, for example, intravenous solution, sprays, Band-Aids or pills.

In a further aspect thereof, the present invention is directed at a pharmaceutical formulation—produced as above—for the treatment or prevention of the metabolic syndrome or its complications, characterized in that it comprises Mas-G-protein-coupled receptor agonists and pharmaceutically and pharmacologically acceptable carriers. Preferably, said pharmaceutical formulation is characterized in that it is present in the form of an implantable, injectable or orally administrable micro- and nano-particulated device. The amount of the agonists in the composition to be administered should be an amount sufficient and appropriate to provide a plasma concentration of the antagonist in the range of $10^{-10}$ to $10^{-6}$ molar.

In a final aspect thereof, the present invention is directed at the use of an agonist of the Mas-G-protein-coupled receptor for the production of a medicament for the treatment of metabolic syndrome and related conditions as described herein.

Divergent Signaling Routes in the Metabolic Syndrome Related to the RAS

Cardiovascular and renal complications are leaders in the morbidity in patients with diabetes. The insulin-resistance/hyperglycemia/Ang II triad is closely involved in the pathogenesis of the lesions of the target-organs [Carey R M and Siragy H M. The intrarenal renin-angiotensin system and diabetic nephropathy. *Trends Endoc Metab,* 14 (6): 274-281.

Thus, like other growth factors, insulin stimulates the MAPK pathway. The cascade begins with the phosphorylation of IRS and/or Shc proteins, which interact with the Grb2 protein, constitutively associated to the SOS, a protein that as a result activates the Ras, a small G protein. The Ras triggers the sequential phosphorylation of the cascade of the MAPKs, leading to the cellular proliferation and differentiation [Marrero M B, Fulton D, Stepp D, Stern D M. Angiotensin II-induced insulin resistance and protein tyrosine phosphatases. *Arterioscler Thromb Vasc Biol* 24:2009-2013, 2004].

On the other hand, the responses of Ang II in the vascular cells are mediated by various and complex effector systems of the plasma membrane, such as: phospholipase (A, C and D), adenylcyclase, PKC and ionic channels that are activated in conjunction with a number of proteic microdomains formed chiefly by adaptive proteins.

These proximal pathways lead, for the most part, to the activation of cascades such as Ras/MAPK/ERK and JAK/STAT, which amplify the signal and extend as far as the nucleus, regulating the gene expression and stimulating the cellular proliferation [Touyz R M. Reactive oxygen species as mediators of calcium signaling by angiotensin II: implications in vascular physiology and pathophysiology. Antioxid Redox Signal. (9-10):1302, 2005; Watanabe T, Barker T A, Berk B C. Angiotensin II and the endothelium: diverse signals and effects. Hypertension. 45(2):163-9, 2005; Touyz R M. Reactive oxygen species, vascular oxidative stress, and redox signaling in hypertension: what is the clinical significance? Hypertension. 44(3):2248-52, 2004].

In addition, Ang II stimulates the TGF-β, an important mediator of the formation of collagen and, therefore, of the deposition of extracellular matrix and fibrosis, the main causes of diabetic nephropathy [Carey R M; Siragy H M, The intrarenal renin-angiotensin system and diabetic nephropathy. *Trends Endocrin. Metabol.* 14(6): 274-281, 2003]. In turn, hyperglycemia reinforces the vasoconstrictive and proliferative actions of Ang II, increasing the vascular hyperplasia and progression of nephrophathy.

Antagonists that can influence directly or indirectly the activation of these cascades have been considered an important strategy for the treatment of the cardiovascular complications in the DM, and the antagonists of the RAS have already demonstrated that they attenuate the progression of the lesions of the target-organs [Carey R M and Sragy H M. The intrarenal renin-angiotensin system and diabetic nephropathy. *Trends Endocrin. Metabol.* 14(6): 274-281, 2003]. One of the few data in the literature referring to the mechanisms of intracellular action of Ang-(1-7) is provided by Tallant and Clark, 2003 [Tallant E A, Clark M A. Molecular mechanisms of inhibition of vascular growth by angiotensin-(1-7). *Hypertension.* October; 42(4):574-9, 2003] demonstrating exactly that the antiproliferative effects of Ang-(1-7) on the vascular smooth muscle are related with the inhibition of the activity of the ERK1/2 (p44/42 MAPK).

However, in the prior art there is no application of the use of Mas-G-protein-coupled receptor agonists in the treatment of the metabolic syndrome, its components and its complications.

Ang II stimulates the association and translocation of the cytoplasmatic subunits of the NAD(P)H oxidase (p47phox, p67phox and p40phox), resulting in activation of this enzyme, which is the greatest source of superoxide ions in the vasculature. The formation of reactive oxygen species seems to be one of the main mechanisms by which Ang II alters the signaling of insulin. In addition, the insulin resistance leads to the superexposure of the AT1 receptors, potentiating the formation of free radicals in the vessels.

Another essential pathway in the signaling of insulin is that of phosphatidyl-inositol 3-kinase (PI3-K). The phosphorylation of IRS-1 creates recognition sites for molecules with SH2 domains, such as PI3k. The PI3-K is important in the regulation of mitogenesis, in the cellular differentiation and essential to the transport of glucose stimulated by insulin. The phosphatidilinositol-3,4,5-triphosphate generated by the PI3K regulates PDK-1 ("phosphoinositide-dependent kinase 1"), a serine/threonine kinase that phosphorylates and the protein kinase B (PKB)/Akt [Sowers J R, Insulin resistance and hypertension. *Am J Physiool Heart Circ Physiol.* 286(5): H1597-1602, 2004].

Recently, it was demonstrated that, in addition to the classical pathway dependent on calcium, the formation of nitric oxide can be modulated through direct phosphorylation of specific amino acids of the synthesis of endothelial NO. The phosphorylation of serine 1177 by the protein kinase B/Akt, increases the enzymatic activity and the production of nitric oxide (NO) [Fulton D, Gratton J P, McCabe T J, Fontana J, Fujio Y, Walsh K, Franke t f, Parapetropoulos A, Sessa W C; Regulation of endothelium-derived nitric oxide, production by the protein kinase Akt. *Nature,* 10; 399(6736):597-601, 1999).

The ability of insulin to increase the generation of NO has already been demonstrated in culture of endothelial cells. Another vasodilator mechanism of insulin and IRS-1 dependent on the PI3K pathway is the reduction of [Ca2+) through the increase of the activity of the pump $Na^+$—$K^+$-ATPase on the smooth muscle [Sowers J R, Insulin resistance and hypertension. *Am J Physiol Heart Circ Physiol.* 286(5): H1597-1602, 2004]. This action also includes desensitization of the binding $Ca^{2+}$-MLC ("myosin light-chain"). Some data in the literature suggest that Ang II acting on AT1 receptor inhibits the vascular action of insulin, interfering with the cascade of the PI3K, reducing the availability of NO. This alteration in the PI3K pathway also alters the use and transport of glucose. It was also demonstrated that the increase in Ang II levels is associated to alteration in the GLUT4.

The action of insulin is also attenuated by proteins tyrosine phosphathases (PTPases), which catalyzes the rapid dephosphorylation of the insulin receptor and its substrates. The PTP1B seems to be an important phosphathase in this desensitization, since mice with genetic deletion for PTP1B have an increase in the phosphorylation in tyrosine of the insulin receptor and consequently exhibit higher insulin sensitivity, keeping euglycemic with half of the insulin levels with respect to the wild species. In addition, these animals are resistant to obesity induced by diet.

Ang II induces the activation of PTP1B, via protein kinase A (PKA), in the vascular smooth muscle; this phosphatase is probable a key molecule in the inhibition of the insulin signaling induced by Ang II [Marrero M B, Fulton D, Stepp D, Stern D M. Angiotensin II-induced insulin resistance and protein tyrosine phosphatases. *Arterioscler Throm Vasc Biol* 24:2009-2013, 2004]. The interference and antagonism of Ang II in the intracellular insulin signaling can explain in part the beneficial effects of the blockage of the RAS in the insulin sensitivity and vascular function in patients with MS.

Clinical Treatment of Metabolic Syndrome

The treatment of the metabolic syndrome should extend the care to each of the modifiable risk factors that promote the syndrome, like overweight and obesity, sedentary lifestyle and atherogenic diets.

The behavioral modification, represented by loss of weight and by physical exercises, is the first-line therapy. The medicament treatment for each of the components of the syndrome should be present, if one does not achieve the therapeutic targets for the reduction of cardiovascular morbid-mortality with change of habits alone.

The inhibition of the RAS through the use of the ACE (ACEi) inhibitors and the Ang II receptor blockers (ARB) have been extensively studied in the treatment of hypertension, cardiac insufficiency, coronary artery disease and renal diseases. Both groups of drugs consistently reduce the risk of coronary events, cerebrovascular accident (CVA) and microvascular complications of DM. In addition, numerous studies have demonstrated the reduction in the incidence of type-2 diabetes.

However, in the prior art there are no applications of the use Mas, G-protein-coupled receptor agonists in the treatment of the metabolic syndrome, its components and its complications.

The ACEi increase insulin sensitivity on insulin-resistant models of both animals and humans [Jauch K W, Hartl W, Guenther B, Wicklmayer M, Rett K, Dietze G; Captopril enhances insulin responsiveness of forearm muscle tissue in non-insulin-dependent diabetes mellitus. *Eur J. Clin Invest.* 17(5):448-454, 1987], reducing the production of Ang II. Various mechanisms are implied in this finding, but they are not totally understood. The role of bradykinin (BK) was observed by Carvalho et al [Carvalho C R, Thirone A C, Gontijo J A, Velloso L A, Saad M J; Effect of catopril, losartan, and bradykinin on early steps of insulin action. Diabetes; 46(12):1950-1957], which describe, after acute administration of captopril to rats, an increase in the insulin receptors induced by insulin and an increase in the phosphorylation of IRS-1 (insulin receptor substrate 1), in the liver and in the muscles. These procedures were accompanied by the increase in the IRS-1/pi3-kinase in both tissues. The PI3kinase is necessary for the translocation of GLUT1 and for the stimulation of GLUT4, in addition to the metabolism of glycogen [Czech M P, Corvera S.; Signaling mechanisms that regulate glucose transport. J Biol. Chem. 22; 274(4):1865-1868, 1999]. It is believed that the IRS-1/pi3-kinase is linked to the muscular glucose transport, as well as to the synthesis of glycogen in the liver and muscles, and that the increase is this association, in animals treated acutely with captopril, can improve insulin sensitivity. In addition, this medicament inhibits the kinase II (an enzyme similar to the ACE, which acts degrading the BK), consequently generating an increase in its concentrations.

However, in the prior art there are no applications of the use Mas, G-protein-coupled receptor agonists in the treatment of the metabolic syndrome, its components and its complications.

The literature has indicated that the administration of BK improves the action of insulin and reduces the plasma levels of glucose [Uehara M, Kishikawa H, Isami S, Kisanuki K, Ohkubo Y, Miyamura N, Miyata T, Yano T, Shichiri M; Effect on insulin sensitivity of angiotensin converting enzyme inhibitors with or without a suphydryl group: bradykinin may improve insulin resistance in dogs and humans. *Diabetologia*. 37(3):300-307, 1994]. Again, the study by CARVALHO et al (1997) [Carvalho C R, Thirone A C, Gontijo J A, Velloso L A, Saad M J; Effect of captopril, losartan and bradykinin on early steps of insulin action. Diabetes; 46(12):1950-1957, 1997], demonstrated that BK increases the number of receptors induced by insulin and the phosphorylation of IRS-1, as well as the association IRS1/PI3 kinase in the liver and in the muscles, improving insulin sensitivity.

In addition to the use of the ACEis and of the ABRs, Ang-(1-7) may be considered a potential candidate for therapeutic use, since this peptide is capable of inducing the production of NO and prostaglandins 12, of modulating the actions of Ang II, as well as potentiating the reduction of the blood pressure through the ACEi.

Clinical Studies Related to the Inhibition of RAS and Metabolic Syndrome

1. Studies Related to the Reduction of the Incidence of Diabetes:

In the HOPE (Heart Outcomes Prevention Evaluation) study, the incidence of diabetes was 34% lower in the group treated with ramipril than in the group that received placebo [Yusuf S. Sleight P, Pogue J, Bosch J, Davies R, Dagenais G.; Effects of an angiotensin-converting-enzyme inhibitor, ramipril, on cardiovascular events in high-risk patient. The Heart Outcomes Prevention Evaluation Study Investigators. N Engl J. Med. 20; 342(3):145-53, 200. Erratum in: 4; 432(18):1376, 2000. N Engl J. Med 9; 342(10):748]. In the LIFE study (Losartan Intervention for Endpoint Reduction in hypertension study) [Lindholm L H, Ibsen H, Dahlof B, Devereu R B, Beevers G, by Faire U, Fyhrquist F, Julius S, Kjeldsen S E, Kristiansson K, Lederballe-Pedersen O, Nieminen M S, Omvik P, Oparil S, Wedel H, Aurup P, Edelman J, Snapinn S; LIFE Study Group; Cardiovascular morbidity and mortality in patients with diabetes in the Losartan Intervention for Endpoint reduction in hypertension study (LIFE): a randomized trial against atenolol. Lancet. 23; 359(9311):1004-10, 2002] Losartan was associated with reduction of 25% in the appearance of new cases of diabetes when compared with atenolol. The same thing occurred when comparing patients in use of candesartan with those in use of hydrochlorotiazide for the treatment of arterial hypertension, with a significant reduction in the incidence of type-2 diabetes. The results of the VALUE study also indicate a 23% reduction in new cases of diabetes, when compared with hypertensive patients treated with valsartan and amlodipine [Julius S, Kjeldesen S E, Weber M, Brunner H R, Ekman S, Hansson L, Hua T, Laragh J, McInnes G T, Mitchell L, Plat F, Schortk A, Smith B, Zanchetti A; VALUE trial group; Outemes in hypertensive patients at high cardiovascular risk treated with regimens based on valsartan or amlodipine: the VALUE randomized trial. Lancet. 19; 363(9426):2022-31, 2004].

On the other hand, the CAPP (Cognition and Prognosis in the Elderly by the Captopril Prefention Project) study and STOP-HTN (Cardiovascular Events in Elderly Patients with Isolated Systolic Hypertension) study did not show any significant difference in the reduction of the incidence of diabetes when compared with ACEi and ARB [Vijayaraghavan K, Deedwania P C; The renin angiotensin system as a therapeutic target to prevent diabetes and its complications. Cardiol Clin. 23(2):165-83, 2005].

Possible mechanisms responsible for the reduction in incidence of type-2 diabetes in these studies are the improvement of the capitation of insulin-mediated glucose, improvement in the endothelial function, increase in the activation of NO, reduction in the inflammatory response and increase in the levels of bradykinin and Ang-(1-7) [Vijayaraghavan K, Deedwania P C; The renin angiotensin system as a therapeutic target to prevent diabetes and is complications. *Cardiol Clin.* 23(2):165-83, 2005].

2. Studies Related to Insulin Resistance

The inhibition of ACE improves the sensitivity to insulin, also permitting, in some cases, the withdrawal of the sulfonylurea and reduction in the doses of insulin [De Mattia G, Ferri C, Laurenti O, Cassone-Faldetta M, Piccoli A, Santucci A; Circulating catecholamines and metabolic effects of captopril in NIDDM patients. Diabetes CAr; 19(3):226-30, 1996]. Various studies have confirmed these data, through clamps for evaluation of the sensitivity to insulin, as for instance that by Paolisso in 1992, who compared lisinopril and Placebo, that by Vuorinne-Markkola in 1995, who compared enalapril and placebo, that by Falkner in 1995, comparing lisinopril and placebo, that by Fogarl in 1998, who evaluated losartan by comparing it with placebo, that by Higashiura in 1999, who compared candesartan (ARB) with placebo, among others [Vijayaraghavan K, Deedwania P C; The renin angiotensin system as a therapeutic target to prevent diabetes and is complications. *Cardiol Clin.* 23(2):165-83, 2005].

Patients carrying DM or the metabolic syndrome have an increased risk of cardiovascular and renal diseases. Both the DM and the metabolic syndrome are multifactor diseases and, therefore, need an approach to various of their risk factors such as glycemic control, anti-platelet-aggregating agent, lipid-profile control and pressoric-level control. The benefit of the pressoric-level control in patients with diabetes has been demonstrated in various clinical studies, chiefly through the use of RAS blockers. The therapeutic use of this class of pharmaceuticals in carriers of the metabolic syndrome has reduced the morbidity-mortality risk as one attempts to reduce the incidence of type-2 diabetes in these patients.

EXAMPLES

The present invention will now be further explained in the following examples without being limited thereto with further reference to the accompanying figures. For the purposes of the present invention, all references as cited are incorporated by reference in their entireties.

EXAMPLE 1

This Example Describes the Effect of Deletion of Mas on the Body Weight of Knock-Out FVBN Mice (Ko-Mas)

By molecular biological techniques, the gene responsible for the synthesis of Mas was deleted in mice of the FVBN line, for its use as a tool for the evaluation of the role of Ang-(1-7) via Mas. Knock-out FVBN animals (Ko-Mas) and Wild-type FVBN (WT-FVBN) control animals at an age between 9 and 10 weeks were kept under conditions of stable temperature and half-day light cycle with plenty of food and water.

A total of 15 WT-FVBN animals and the 19 of Ko-Mas were weight on a semi-analytic scale for analysis of the total body weight. The result was analyzed statistically by using the unpaired Student's t test, the results that presented $P<0.05$ being considered significant.

Figure 1:
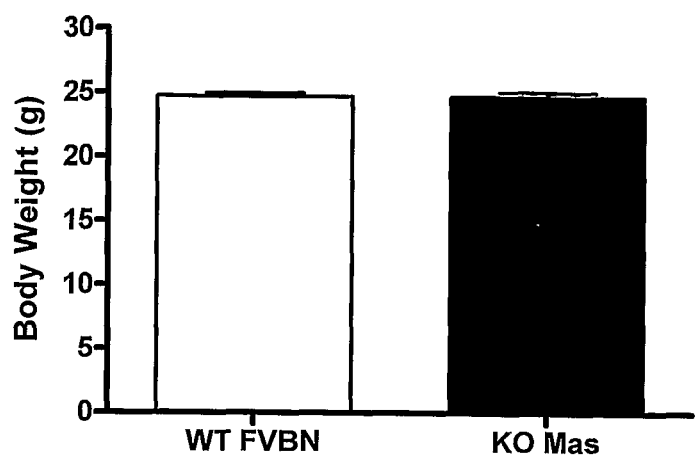
FIG. 1 shows that genetic deletion of Mas did not change the body weight of young (≤10 weeks old) mice (Example 1).

No significant difference between the groups were observed (FIG. 1).

EXAMPLE 2

Presence of Mas in the Adipose Tissue and Effect of Mas Deficiency on the Fat Tissue Mass This example describes the expression of Mas mRNA in fat tissue and the effect of Mas deficiency on the fat tissue mass (adipose tissue weight).

Figure 18:
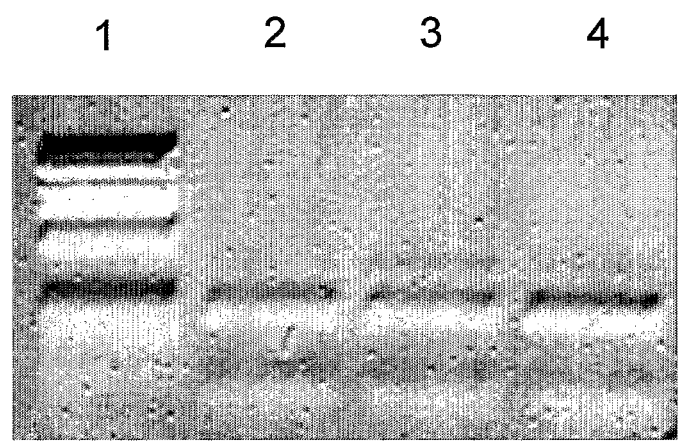
FIG. 18 shows the Mas mRNA expression in adipose tissue of WT mice and SD rat (Example 2).

Sprague-Dawley rats (n=3) and WT mice (n=3) mice were used for RT-PCR studies. After anesthesia [ketamine (130 mg/kg) and xylazine (0.3 mg/kg)] and blood collection, they were sacrificed for removal of epididymal white adipose tissue. Total mRNA was extracted and processed as described in example 11. As shown in FIG. 18 Mas mRNA is expressed in mice and rat adipose tissue.

Figure 2:
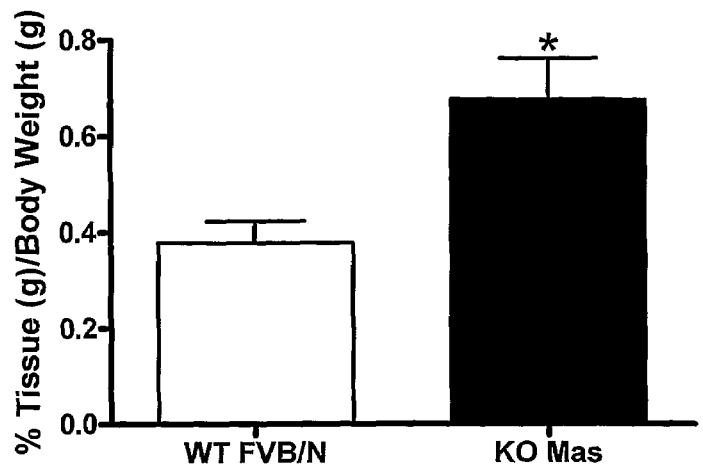
FIG. 2 shows that although genetic deletion of Mas in FVBN mice did not produced an increase in body weight (FIG. 1) it substantially increase the fat tissue mass (Example 2).
Figure 2:
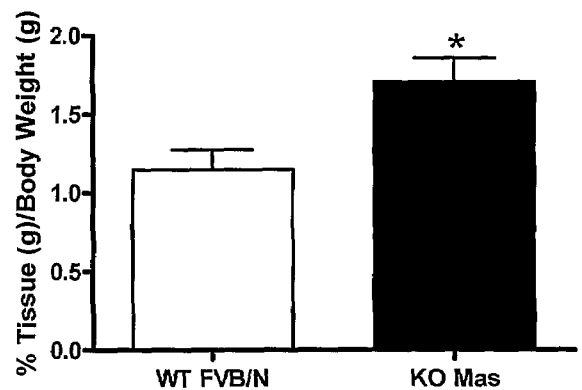
Figure 2:
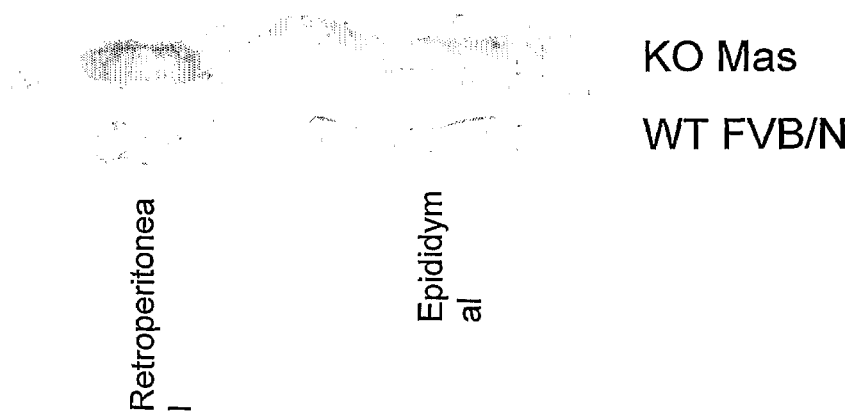

Effect of Mas deletion on fat tuissue. The WT-FVBN (n=6) and Ko-Mas (n=6) mice were weighed in a semi-analytic scale to quantify the total body weight. After anesthesia [ketamine (130 mg/kg) and xylazine (0.3 mg/kg)] and blood collection, they were sacrificed for removal of epididymal and retroperitoneal white adipose tissue. The tissues were weighted in a semi-analytical scale and the weight was corrected by the total body weight. The result are shown in percent of body weight and analyzed using non-paired student t test. A Value of $P<0.05$ was considered significant. As shown in FIG. 2, genetic deletion of Mas in FVBN mice produced an increase in the fat tissue mass. These changes can be a direct consequence of lock of Mas in adipose tissue.

EXAMPLE 3

Effect of Chronic Increase in Plasma Levels Angiotensin-(1-7) on the Body Weight This example describes the effect of chronic increase in plasma levels angiotensin-(1-7) on the body weight, using transgenic rats that express an angiotensin-(1-7)-producing fusion protein.

Figure 3:
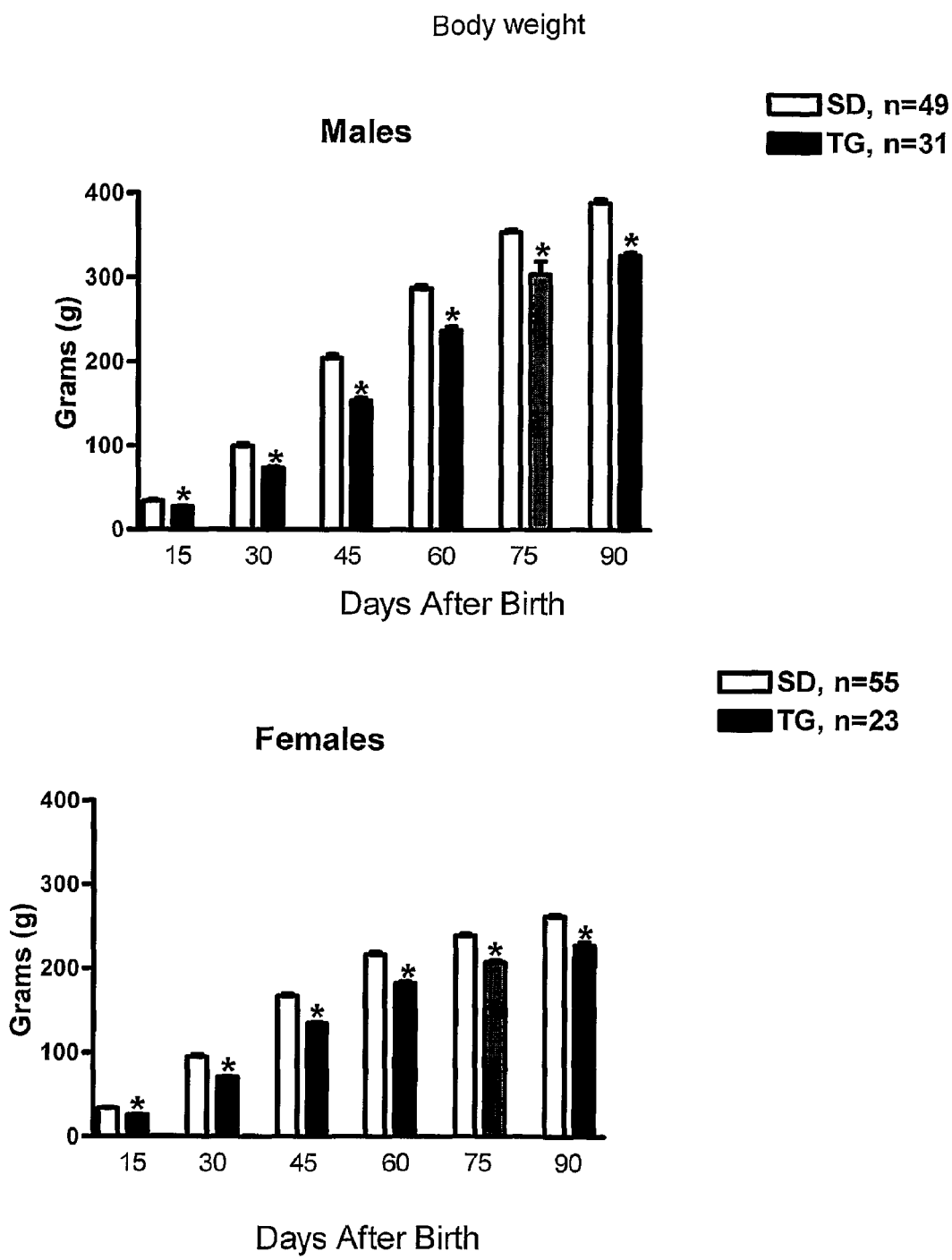
FIG. 3 shows that a significant lower body weight in TG rats was observed at all ages in example 3.

The body weight of transgenic rats (TGR(A1-7)L3292) which present an increase in the angiotensin-(1-7) plasma levels (approximately 2.5-fold) was measured after 15, 30, 45, 60, 75 and 90 days of birth. The values were compared with those obtained in age-matched controls, Sprague Dawley rats. A significant lower body weight in TG rats was observed at all ages (FIG. 3). This observation, which could not be explained by changes in food intake or water balance (data not shown), suggests that chronic administration of angiotensin-(1-7) or other receptor Mas agonists may decrease body fat.

EXAMPLE 4

Effect of the Deletion of Mas on the Levels of Total Blood Cholesterol and HDL in Knock-Out Mice This example describes the effect of the deletion of Mas on the levels of total blood cholesterol and HDL of Knock-out FVBN mice for Mas gene (Ko-Mas).

A total of six WT-FVBN and the same number of Ko-Mas were put on a 12-hour fasting condition before the experiment; then they were anesthetized with Ketamin (4.5 mg/Kg)+Xylazin (0.2 mg/Kg), and an abdominal incision was made for exposure of the aorta artery. The collection of the arterial blood was made from a cut in the aorta artery, close to the renal branching, the blood being collected through a Pasteur pipette.

The blood was then centrifuged, and one obtained a plasma fraction that was used for the dosage according to the specifications of the manufacturer of the Kit. The reading was effected on a spectrophotometer in the 492-nm wavelength for dosage of total cholesterol and HDL. The result was analyzed statistically by using the unpaired Student's t test, with results that exhibited $P<0.05$ being considered significant.

Figure 4:
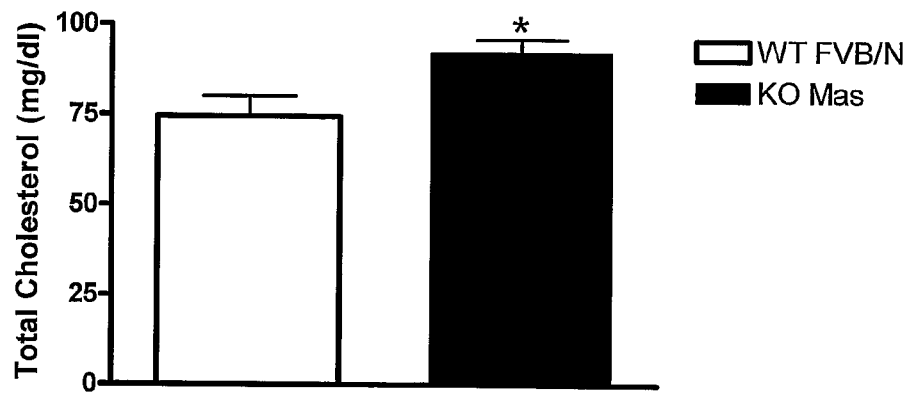
FIGS. 4 and 5 show that the deletion of Mas increases the levels of total blood cholesterol and HDL in animals, compared to control animals (Example 4).
Figure 5:
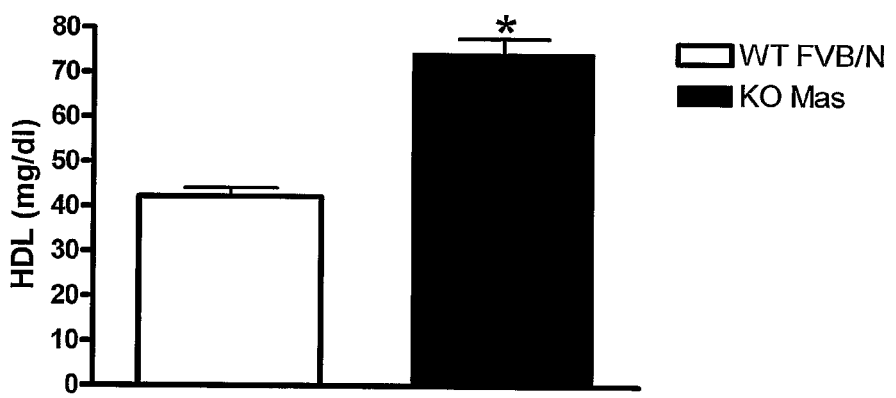

A significant difference between the groups was observed, showing that the deletion of Mas increases the levels of total blood cholesterol and HDL in these animals when compared with the control animals (FIGS. 4 and 5).

This result shows that the genetic deletion of Mas alters the metabolism of the animal, causing an increase in the levels of total cholesterol and HDL, thus indicating the participation of the Mas/Ang-(1-7) axis in the metabolic regulation of cholesterol.

EXAMPLE 5

Effect of the Deletion of Mas on the Blood Levels of Triglycerides of Knock-Out Mice This example describes the effect of deletion of Mas on the blood levels of triglycerides of Mas Knock-out FVBN mice (Ko-Mas).

A total of six WT-FVBN animals and the same number of Ko-Mas were put on a 12-hour fasting condition before the experiment; then they were anesthetized with Ketamin (4.5 mg/Kg)+Xilazin (0.2 mg/Kg), and an abdominal incision was made for exposure of the aorta artery. The collection of the arterial blood was made from a cut in the aorta artery, close to the renal branch, and blood was collected through a Pasteur pipette.

The blood was then centrifuged, and one obtained a plasma fraction that was used for the dosage according to the specifications of the manufacturer of the Kit.

Figure 6:
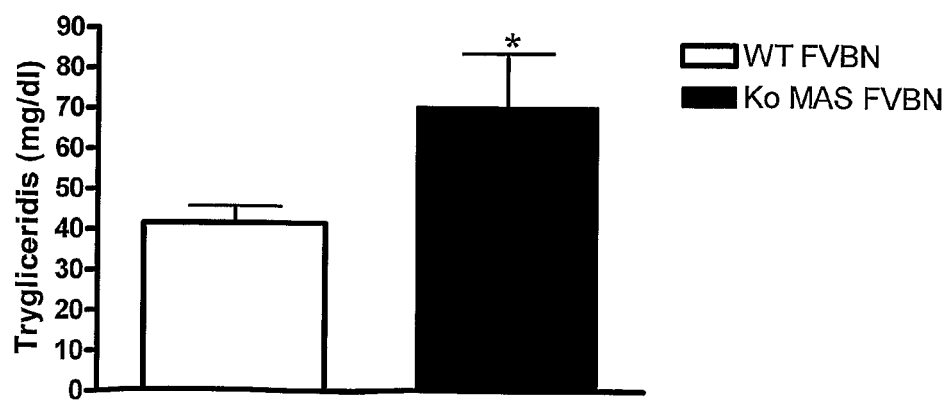
FIG. 6 shows that the deletion of Mas alters the blood levels of triglycerides in animals compared to control animals (Example 5).

The reading was effected on a spectrophotometer in the 500-nm wavelength for dosage of the triglycerides. The result was statistically analyzed with the unpaired Student's t test, results that exhibited $P<0.05$ being considered significant. A significant difference between the groups was observed, showing that deletion of Mas increase the blood levels of triglycerides in these animals when compared with the control animals (FIG. 6).

This result shows that genetic deletion of Mas alters the metabolism of the animal, causing an increase in the levels of triglycerides, thus indicating the participation of the Mas/Ang-(1-7) axis in the metabolic regulation of triglycerides.

EXAMPLE 6

Effect of the Deletion of Mas on Insulin Resistance in Knock-Out Mice

This example describes the effect of deletion of Mas on insulin resistance in Mas Knock-out FVBN mice (Ko-Mas).

A total of six WT-FVBN animals and the same number of Ko-Mas mice were used, which had been fed. The test began with a measurement of basal glycemia, for which a little cut was made at the tip of the animal's tail for collection of a drop of blood and measurement of the plasma concentration of glucose with the help of a glycosimeter.

After intraperitoneal application of insulin at a dose of 0.75 IU/Kg of body weight glycemia was measured at 15, 30 and 60 minutes.

The statistic analysis was carried out by using the Two Way ANOVA test, and results exhibiting $P<0.05$ were considered significant.

Figure 8:
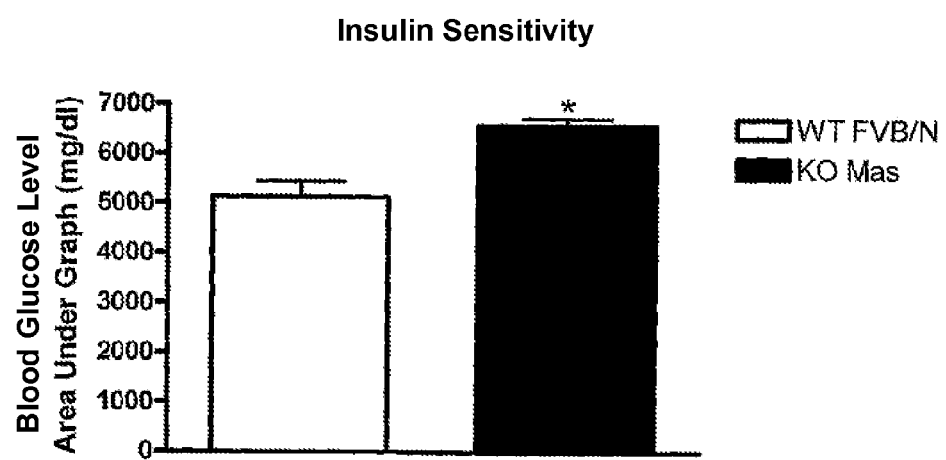
FIGS. 8 and 9 show that Mas KO animals have low insulin sensitivity, both when the area under the graph along the time (FIG. 8) is analyzed and when a point-to-point analysis along the time (FIG. 9) is made. All results are statistically different (Example 6).
Figure 9:
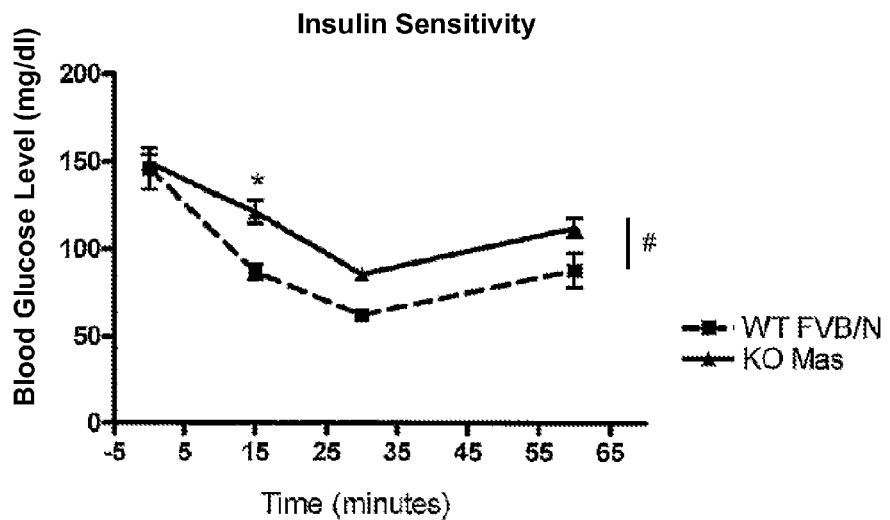

The results showed that the Ko-Mas animals have higher insulin resistance, both when the area under the graph along the time (FIG. 8) is analyzed and when one makes a point-to-point analysis along the time (FIG. 9). All the results were statistically different.

These data show that genetic deletion of Mas alters the tissular resistance to glucose, causing an increase in the glycemic levels, thus indicating the participation of the Mas/Ang-(1-7) axis in the metabolic regulation of insulin and its receptors.

EXAMPLE 7

Effect of Deletion of Mas on the Tolerance to Glucose in Knock-out Mice

This example describes the effect of deletion of Mas on the tolerance to glucose in Mas Knock-out FVBN mice (Ko-Mas).

A total of six WT-FVBN animals and the same number of Ko-Mas were put on a 12-hour fasting condition before the experiment. The test began with a measurement of fasting glycemia, for which a little cut was made at the tip of the animal's tail for collection of a drop of blood and measurement of the plasma concentration of glucose with the aid of a glycosimeter.

After intraperitoneal application of glucose at the dose of 2 g/Kg of body weight glycemia was measured at 15, 30, 60 and 120 minutes.

The statistic analysis was carried out by using the Two Way ANOVA test, the results that exhibited $P<0.05$ being considered significant.

Figure 7:
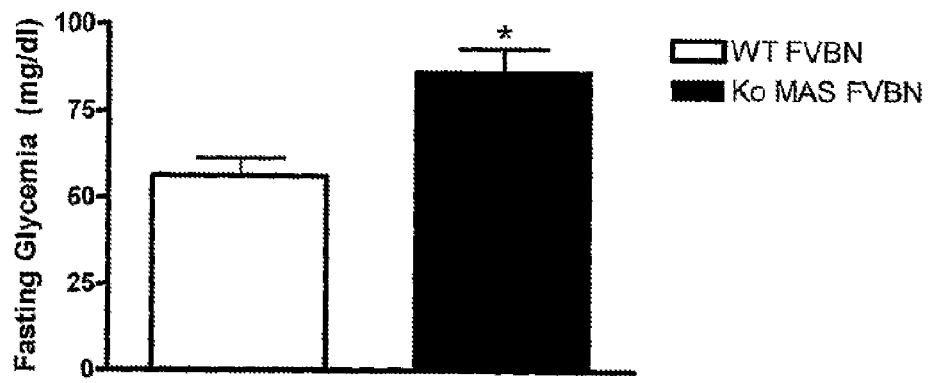
FIGS. 7, 10 and 11 show that Ko-Mas animals exhibit fasting glycemia greater than the control group (FIG. 7) and impaired tolerance to glucose, both when the area under the graph along the time (FIG. 10) is analyzed and when a point-to-point analysis along the time (FIG. 11) is made. All results are statistically different (Example 7).
Figure 10:
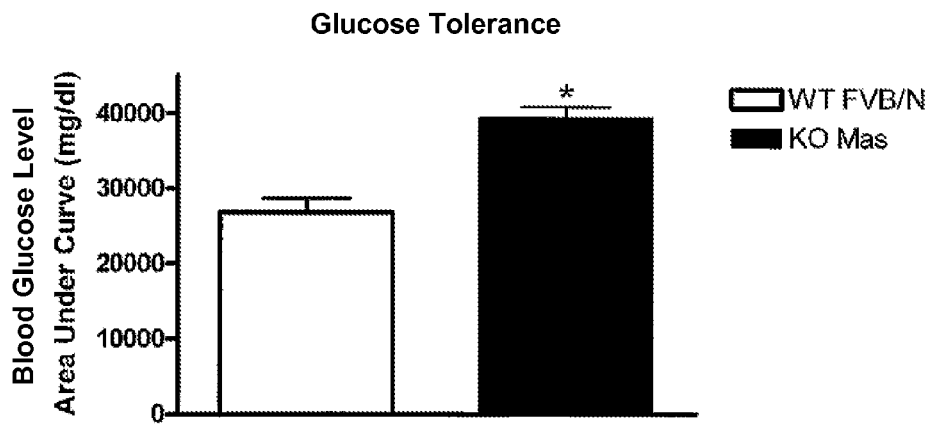
Figure 11:
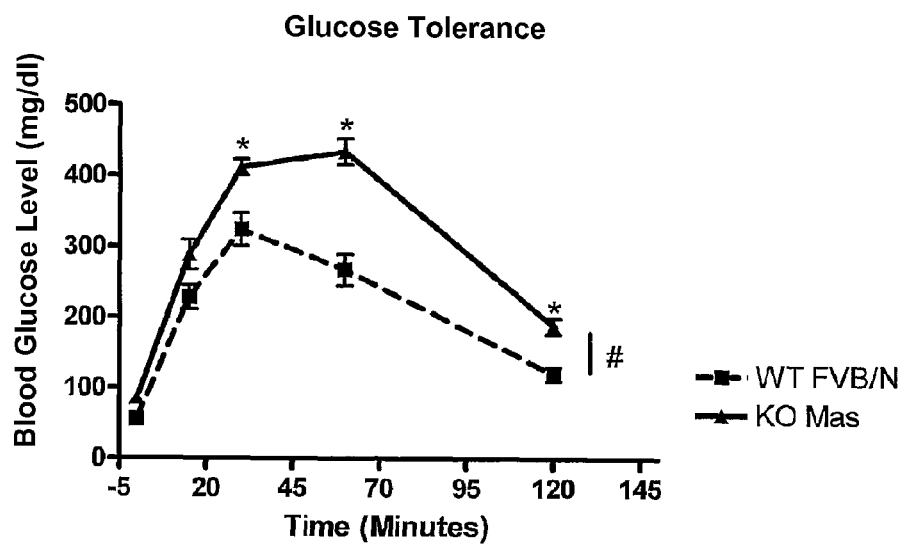

The results showed that the Ko-Mas animals exhibit fasting glycemia greater than the control group (FIG. 7) and impaired tolerance to glucose, both when the area under the graph along the time (FIG. 10) is analyzed and when a point-to-point analysis along the time (FIG. 11) is made. All the results were statistically different.

These data show that genetic deletion of Mas alters the tolerance to glucose, causing an increase in the glycemia levels, thus indicating the participation of the Mas/Ang-(1-7) axis in the metabolic regulation of glucose.

EXAMPLE 8

Effect of Deletion of Mas on Blood Pressure and Heart Rate of Knock-out Mice

This example describes the effect of deletion of Mas on the blood pressure and heart frequency of Mas Knock-out FVBN mice (Ko-Mas).

A total of eight WT-FVBN animals and the same number of Ko-Mas were subjected to the measurement of blood pressure, effected by picking up pulsatile pressure signal sent to the pressure transducer connected to the cannula inserted into the abdominal aorta artery through the femoral artery, by the data acquisition system (Biopac System, model MP100, serial 96122386). The pressure oscillations picked up were amplified and converted through an analogical/digital conversion plate into signals that fed the data acquisition plate. Through the plate reading software, Acknowledge v. 3.5.7, the pulsatile blood pressure is collected continuously with a sampling frequency of 2000-4000 Hz. The average blood-pressure values (BPV) and heart frequency (HF) are calculated from the blood-pressure pulses and recorded by the system.

The cannulation of the femoral artery was effected under anesthesia with Ketamine (4.5 mg/Kg)+Xilazine (0.2 mg/Kg), 24 hours before the experimental procedure. After positioning the animal in dorsal decubitus on the operating table, trichotomy of the left inguinal region of the animal was carried out. A small incision in the skin was made by using small scissors. With the help of a magnifying glass, the femoral vasculo-nervous bundle was located and the femoral artery was carefully isolated. The arterial cannula is delicately introduced through the femoral artery as far as the abdominal aorta artery.

The results were statistically analyzed by using the unpaired Student's t test. Results with P<0.05 were considered significant.

Figure 12:
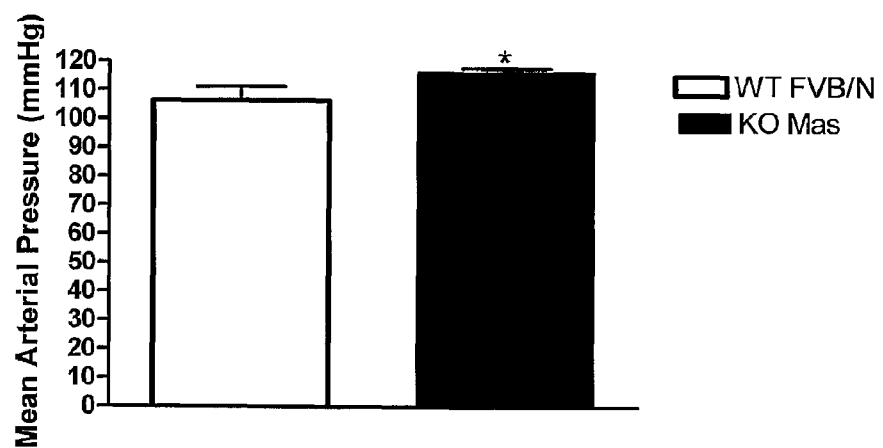
FIGS. 12 and 13 show that the mean arterial blood pressure (MAP) of Ko-Mas animals is significantly higher than of the control animals (WT-FVBN) (FIG. 12). However, the heart rate (HR) values do not differ among the experimental groups (FIG. 13) (Example 8).
Figure 13:
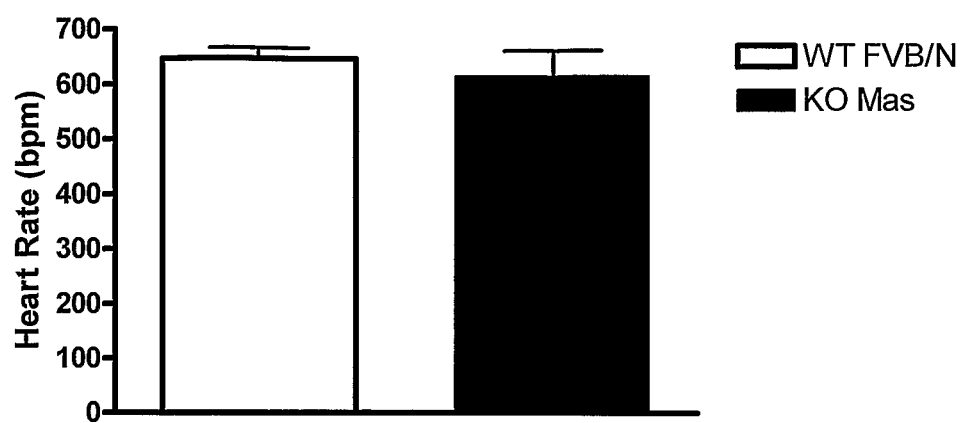

In conjunction, the results show that the mean arterial blood pressure (MAP) of the Ko-Mas animals is significantly higher than that of the control animals (WT-FVBN) (FIG. 12). However, the heart rate (HF) values do not differ among the experimental groups (FIG. 13).

These data show that genetic deletion of Mas alters the basal values of ABP, rendering the animals hypertensive when compared with the control (WT-FVBN) animals, thus indicating the participation of the Mas/Ang-(1-7) axis in the regulation of the blood pressure and genesis of the arterial hypertension.

EXAMPLE 9

Effect of Mas Receptor Deficiency on the Expression of the Glucose Receptor

This example describes the effect of Mas receptor deficiency on the expression of the glucose receptor, Glut-4, on the epididymal adipose tissue.

The WT-FVBN (n=4) and Ko-Mas (n=4) mice were weighed in a semi-analytic scale. After anesthesia [ketamine (130 mg/kg) and xylazine (0.3 mg/kg)] and blood collection, they were sacrificed for removal of epididymal white adipose tissue. Thirty µg of protein extract obtained from the epididymal adipose tissue and fractionated in a polyacrylamide/SDS (PAGE) 12% gel at 100 V for 1.5 h. After the run, the proteins were transferred to a nitrocellulose membrane and incubated with an antibody anti-receptor Glut-4. The result is shown in percent of body weight and analyzed using a non-parametric test.

Figure 14:
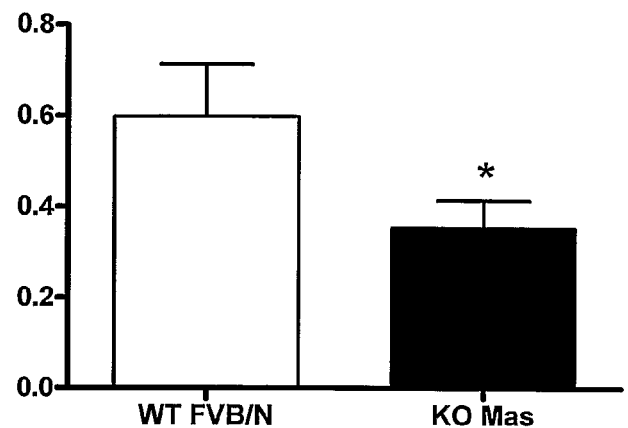
FIG. 14 shows that the genetic deletion of Mas in FVBN mice decreased the Glut-4 expression (Example 9).
Figure 14:
Figure 14:
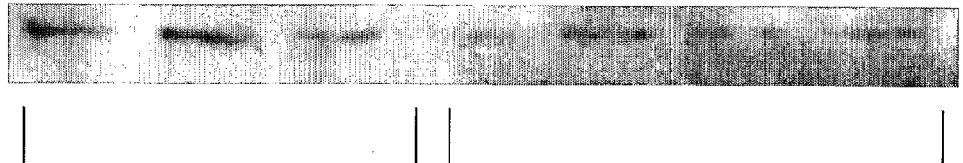

As shown in FIG. 14, genetic deletion of Mas in FVBN mice, decreased the Glut-4 expression, which may be involved in the increase of the glucose plasma levels observed in these animals.

EXAMPLE 10

Effect of Mas Deficiency on the Plasma Levels of Leptin and Adiponectin

This example describes the effect of Mas deficiency on the plasma levels of leptin and adiponectin.

After anesthesia [ketamine (130 mg/kg) and xylazine (0.3 mg/kg)], WT-FVBN (n=10) and Ko-Mas (n=10) were sacrificed for blood collection. The plasma levels of adiponectin and leptin were measured using ELISA Kits.

Figure 15:
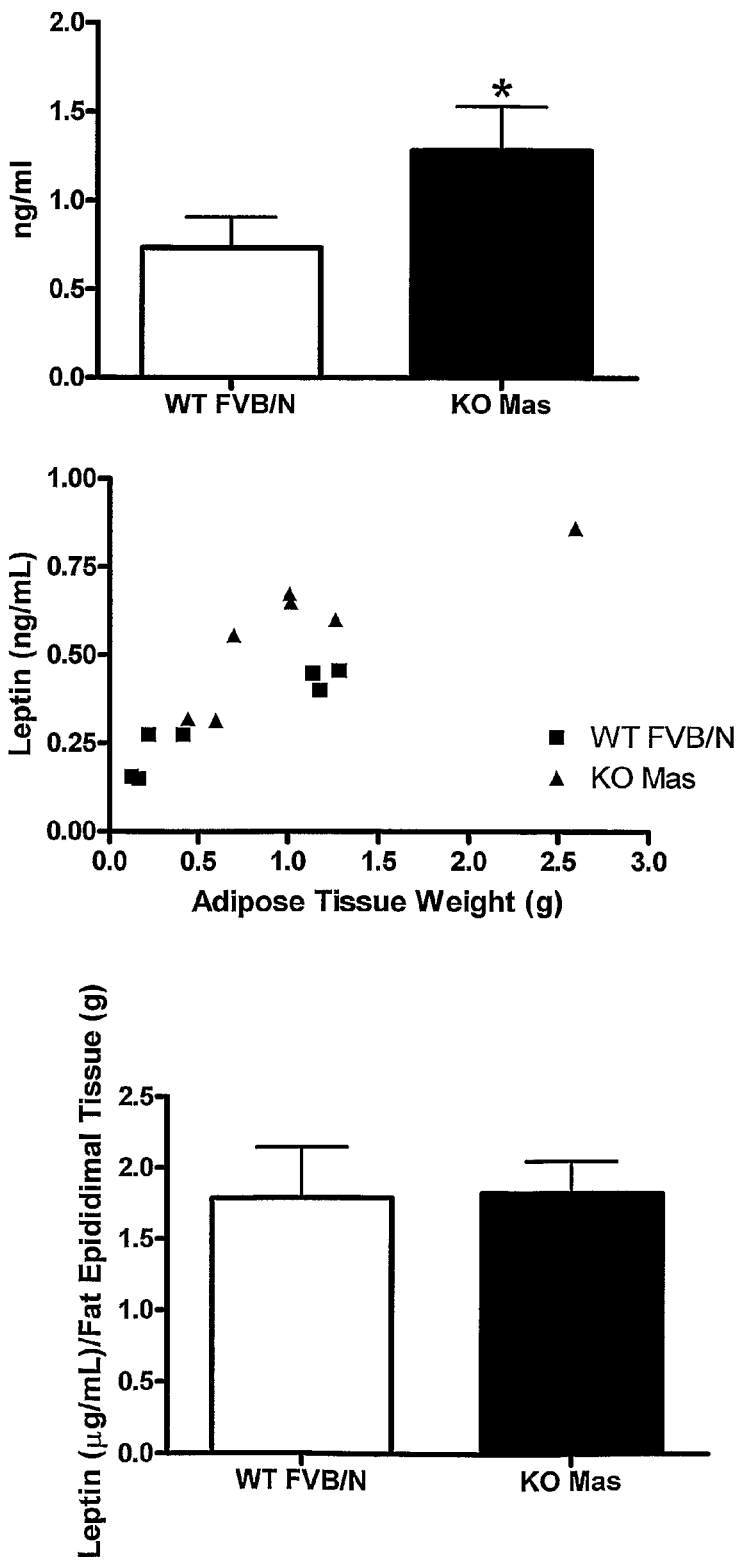
FIG. 15 shows that the leptin plasma levels are increased in Mas-KO Mas mice (Example 10).

The leptin plasma levels are increased in Mas-KO Mas mice (FIG. 15). A close relationship between the alteration in adipose tissue weight and leptin was observed, as shown in FIG. 15. This suggests that the individual adipocyte production is not altered and the increase in plasma levels results from the increase in adipose mass (FIG. 15).

Figure 16:
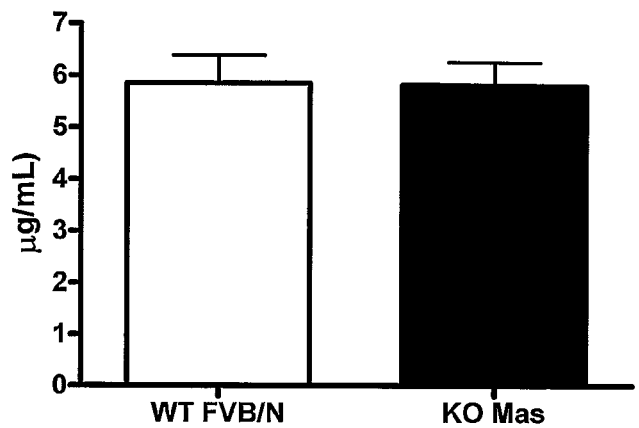
FIG. 16 shows that the adiponectin plasma level are not altered in Mas-KO mice (Example 10).
Figure 16:
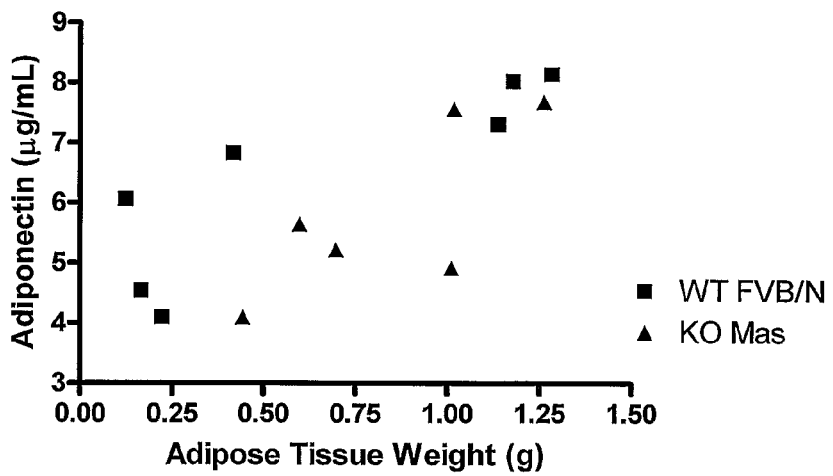
Figure 16:
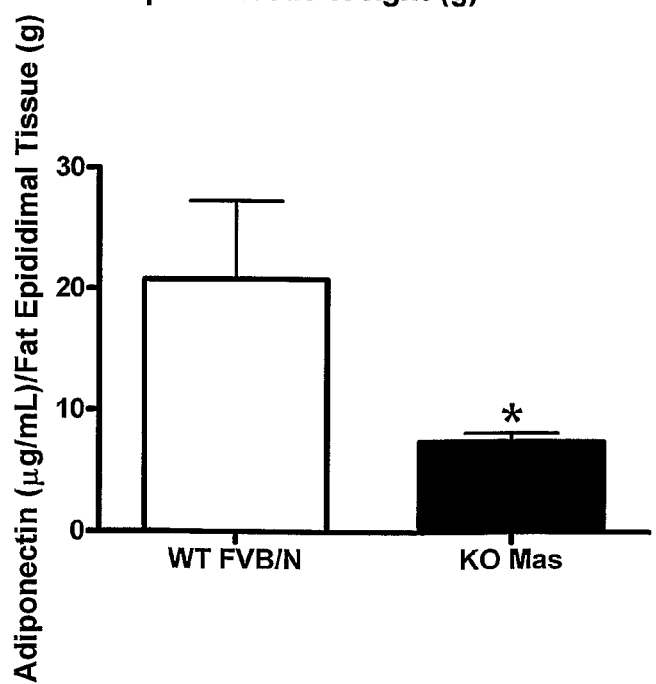

The adiponectin plasma level are not altered in Mas-KO mice (FIG. 16). However, the individual adipocyte production of adiponectin, estimated by normalization of the plasma levels with the fat tissue mass, is decreased in KO (FIG. 16).

EXAMPLE 11

Effect of Mas Deficiency on mRNA Expression of Angiotensinogen and TGF-β from Adipose Tissue This example describes the effect of Mas deficiency on mRNA expression of angiotensinogen and TGF-β from adipose tissue.

After anesthesia [ketamine (130 mg/kg) and xylazine (0.3 mg/kg)], WT-FVBN (n=6) and Ko-Mas (n=6) were sacrificed for adipose tissue collection. The mRNA was extract using Trizol reagent, and the retro transcription was performed using MML-V enzyme. The Real Time PCR was performed on a ABI Prism platform using specific primers for mice angiotensinogen and TGF-β.

Figure 17:
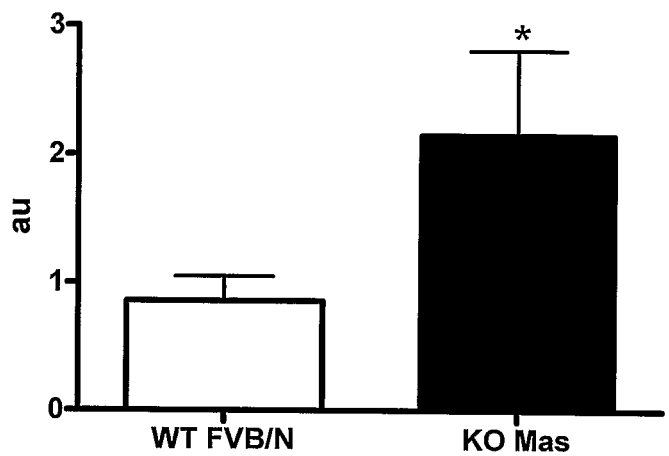
FIG. 17 shows an increase in angiotensinogen and TGF-β mRNA expression in adipose tissue of Mas-KO mice (Example 11).
Figure 17:
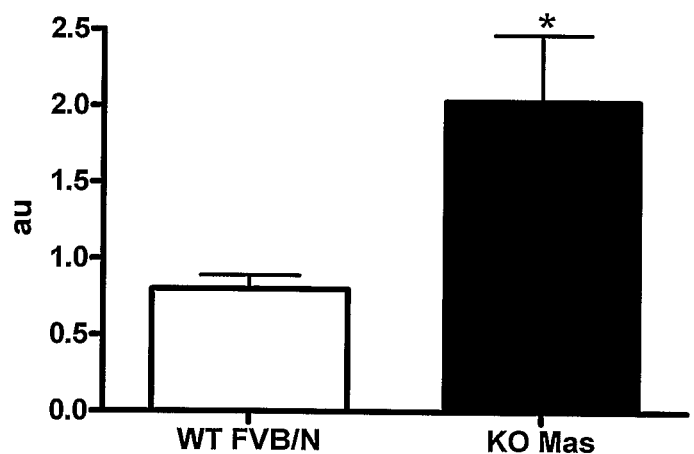

The analyzes revealed an increase in angiotensinogen (FIG. 17) and TGF-β (FIG. 17) mRNA expression in adipose tissue of Mas-KO mice.

In summary, the above examples evidence that the Mas/Ang-(1-7) axis plays an important role in the manifestation of metabolic syndrome, since this deletion, amongst others, led the animals to an, increase in the plasma levels of cholesterol and triglycerides, increase in insulin resistance and in glucose intolerance, increase in fasting glycemia and increase in blood pressure.

The invention claimed is:

1. A method for decreasing blood cholesterol level, decreasing blood glucose level, or both in a subject who has been diagnosed with, and/or has, metabolic syndrome, wherein said method comprises administering, to said subject, an effective amount of angiotensin-(1-7).

2. The method according to claim 1, wherein the angiotensin-(1-7) is administered to said subject in the form of a pharmaceutical formulation via an oral, intramuscular, intravenous, endovenous, subcutaneous, topical, transdermal, anal or inhalation route.

3. The method according to claim 2, wherein the pharmaceutical formulation is administered to said subject in the form of an implantable, injectable, orally administrable micro-particulated, or orally administrable nano-particulated device.

4. The method according to claim 1, wherein the method results in a decrease in the subject's blood cholesterol level.

5. The method according to claim 1, wherein said method results in a decrease in the subject's blood glucose level.

6. The method according to claim 1, wherein the subject has been diagnosed with metabolic syndrome.

7. The method according to claim 1, wherein the subject is a human.

* * * * *